US011905244B2

(12) United States Patent
Zhou et al.

(10) Patent No.: US 11,905,244 B2
(45) Date of Patent: Feb. 20, 2024

(54) CHEMICAL MODULATORS OF STORE-OPERATED CALCIUM CHANNELS AND THEIR THERAPEUTIC APPLICATIONS

(71) Applicant: The Texas A&M University System, College Station, TX (US)

(72) Inventors: Yubin Zhou, Houston, TX (US); Lian He, Houston, TX (US)

(73) Assignee: The Texas A&M University System, College Station, TX (US)

(*) Notice: Subject to any disclaimer, the term of this patent is extended or adjusted under 35 U.S.C. 154(b) by 474 days.

(21) Appl. No.: 17/025,940

(22) Filed: Sep. 18, 2020

(65) Prior Publication Data

US 2021/0139423 A1    May 13, 2021

Related U.S. Application Data

(62) Division of application No. 16/141,656, filed on Sep. 25, 2018, now abandoned.

(60) Provisional application No. 62/563,511, filed on Sep. 26, 2017.

(51) Int. Cl.
*C07D 207/416* (2006.01)
*A61P 35/00* (2006.01)
*A61P 37/06* (2006.01)

(52) U.S. Cl.
CPC .......... *C07D 207/416* (2013.01); *A61P 35/00* (2018.01); *A61P 37/06* (2018.01)

(58) Field of Classification Search
CPC ....... C07D 207/416; A61P 35/00; A61P 37/06
See application file for complete search history.

(56) References Cited

U.S. PATENT DOCUMENTS

2007/0203236 A1* 8/2007 Smith .................. C07D 471/04
514/560

OTHER PUBLICATIONS

Young, K. E., S. Flaherty, K. M. Woodman, N. Sharma-Walia, and J. M. Reynolds, "Fatty acid synthase regulates the pathogenicity of Th17 cells", J Leukoc Biol. (2017), 102(5), pp. 1229-1235. (Year: 2017).*
Ambudkar, I.S., et al., "TRPC1, Orai1, and STIM1 in SOCE: Friends in Tight Spaces," Cell Calcium 63:33-39, 2017.
Berridge, M.J., et al., "Calcium Signalling: Dynamics, Homeostasis and Remodelling," Nature Reviews: Molecular Cell Biology 4:517-529, 2003.
Berridge, M.J., et al., "The Versatility and Universality of Calcium Signalling," Nature Reviews: Molecular Cell Biology 1:11-21, 2000.
Collins, J.K., et al., "Neutralizing Determinants Defined by Monoclonal Antibodies on Polypeptides Specified by Bovine Herpesvirus 1," Journal of Virology 52:403-1984.
Feske, S., et al., "A Mutation in Orai1 Causes Immune Deficiency by Abrogating CRAC Channel Function," Nature 441:179-2006.
Feske, S., et al., "Severe Combined Immunodeficiency Due to Defective Binding of the Nuclear Factor of Activated T Cells in T Lymphocytes of Two Male Siblings," European Journal of Immunology 26:2119-1996.
Franzius, D., et al., "Non-Specific Effects of Calcium Entry Antagonists in Mast Cells," Pflugers Archiv : European Journal of Physiology 428:433-1994.
Gudlur, A., et al., "STIM-ORAI Interactions That Control the CRAC Channel," Current Topics in Membranes 71:33-2013.
Hogan, P.G., et al., "Molecular Basis of Calcium Signaling in Lymphocytes: STIM and ORAI," Annual Review of Immunology 28:491-2010.
Hoth, M., and R. Penner, "Depletion of Intracellular Calcium Stores Activates a Calcium Current in Mast Cells," Nature 355:353-356, 1992.
Ishikawa, J., et al., "A Pyrazole Derivative, YM-58483, Potently Inhibits Store-Operated Sustained Ca2+ Influx and IL-2 Production in T Lymphocytes," Journal of Immunology 170:4441-4449, 2003.
Le Deist, F., et al., "A Primary T-Cell Immunodeficiency Associated With Defective Transmembrane Calcium Influx," Blood 85:1053-1995.
Ohga, K., et al., "The Suppressive Effects of YM-58483/BTP-2, a Store-Operated Ca2+ Entry Blocker, on Inflammatory Mediator Release In Vitro and Airway Responses In Vivo," Pulmonary Pharmacology & Therapeutics 21:360-2008.
Partiseti, M., et al., "The Calcium Current Activated by T Cell Receptor and Store Depletion in Human Lymphocytes is Absent in a Primary Immunodeficiency," The Journal of Biological Chemistry 269:32327-1994.
Putney, J.W., Jr., "A Model for Receptor-Regulated Calcium Entry," Cell Calcium 7:1-1986.
Putney, J.W., Jr., "Pharmacology of Capacitative Calcium Entry," Molecular Interventions 1:84-94, 2001.
Sobolof, J., et al., "STIM Proteins: Dynamic Calcium Signal Transducers," Nature Reviews: Molecular Cell Biology 13:549-565, 2012.
Vig, M., et al., "CRACM1 Is a Plasma Membrane Protein Essential for Store-Operated Ca2+ Entry," Science 312:1220-1223, 2006.
Zhou, Y., et al., "Calciomics: Integrative Studies of Ca2+-Binding Proteins and Their Interactomes in Biological Systems," Metallomics : Integrated Biometal Science 5:29-42, 2013.
Zhou, Y., et al., "Viral Calciomics: Interplays Between Ca2+ and Virus," Cell Calcium 46:1-17, 2009.
Bird, G.S., and Putney, J.W., Jr., "Pharmacology of Store-Operated Calcium Entry Channels," in J.A. Kozak and J.W. Putney, Jr. (eds.), "Calcium Entry Channels in Non-Excitable Cells," CRC Press/Taylor & Francis, Boca Raton, Florida, 2018, pp. 311-324.
Clapham, D.E., "Calcium Signaling," Cell 131:1047-1058, 2007.
Lewis, R.S., "Store-Operated Calcium Channels: New Perspectives on Mechanism and Function," Cold Spring Harbor Perspectives in Biology 3, 2011, pp. 1-26.

(Continued)

*Primary Examiner* — Amanda L. Aguirre
*Assistant Examiner* — Sagar Patel
(74) *Attorney, Agent, or Firm* — Christensen O'Connor Johnson Kindness PLLC

(57) ABSTRACT

Methods of identification of inhibitors of calcium release-activated calcium (CRAC) channel and small molecule inhibitors of CRAC channel, including methods of their synthesis and pharmaceutical use, are disclosed.

23 Claims, 17 Drawing Sheets

Specification includes a Sequence Listing.

(56) References Cited

OTHER PUBLICATIONS

Nguyen, N.T., et al., "Store-Operated Calcium Entry Mediated by ORAI and STIM," Comprehensive Physiology 8:981-1002, 2018.
Parekh, A.B., "Store-Operated CRAC Channels: Function in Health and Disease," Nature Reviews Drug Discovery 9:399-410, 2010.
STN Registry database entry: CAS RN 312266-47-0 (Entered STN: Dec. 29, 2000) (Year: 2000).
STN Registry database entry: CAS RN 903492-08-0 (Entered STN: Aug. 23, 2006). (Year: 2006).
STN Registry database entry: CAS RN 904039-76-5 (Entered STN: Aug. 24, 2006) (Year: 2006).
Bassetto, M., P. Leyssen, J. Neyts, M. Yerukhimovich, D. Frick and A. Brancale, "Comp.-aid. iden., synt. and eval. of subst. thienopyrimidines as novel inhib. of HCV replication" Europ. Journ. Med. Chem. (2016), 123: pp. 31-47. (Year: 2016).
Bassetto, M., P. Leyssen, J. Neyts, M. Yerukhimovich, D. Frick and A. Brancale, "Comp.-aid. iden., synt. and eval. of subst.X thienopyrimidines as novel inhib. of HCV replication" Europ. Journ. Med. Chem. (2016), 123: pp. 31-47 (supplemental information). (Year: 2016).

\* cited by examiner

Boyden chamber invasion assay

Azoxymethane (AOM)-induced mouse colon cancer model

SEQUENCE LISTING

<160> NUMBER OF SEQ ID NOS: 1

<210> SEQ ID NO 1
<211> LENGTH: 299
<212> TYPE: PRT
<213> ORGANISM: Artificial Sequence
<220> FEATURE:
<223> OTHER INFORMATION: Synthetic

<400> SEQUENCE: 1

```
Met His Pro Glu Pro Ala Pro Pro Ser Arg Ser Ser Pro Glu Leu
1               5                   10                  15

Pro Pro Ser Gly Gly Ser Thr Thr Ser Gly Ser Arg Arg Ser Arg Arg
                20                  25                  30

Arg Ser Gly Asp Gly Glu Pro Pro Gly Ala Pro Pro Pro Ser Ala
                35                  40                  45

Val Thr Tyr Pro Asp Gln Ile Gly Gln Ser Tyr Ser Glu Val Met Ser
    50                  55                  60

Leu Asn Glu His Ser Met Gln Ala Leu Ser Trp Arg Lys Leu Tyr Leu
65                  70                  75                  80

Ser Arg Ala Lys Leu Lys Ala Ser Ser Arg Thr Ser Ala Leu Leu Ser
                85                  90                  95

Gly Phe Ala Met Val Ala Met Val Glu Val Gln Leu Asp Ala Asp His
                100                 105                 110

Asp Tyr Pro Pro Gly Leu Leu Ile Ala Phe Ser Ala Cys Thr Thr Val
                115                 120                 125

Leu Val Ala Val His Leu Phe Ala Leu Met Ile Ser Thr Cys Ile Leu
130                 135                 140

Pro Asn Ile Glu Ala Val Ser Asn Val His Asn Leu Asn Ser Val Lys
145                 150                 155                 160

Glu Ser Pro His Glu Arg Met His Arg His Ile Glu Leu Ala Trp Ala
                165                 170                 175

Phe Ser Thr Val Ile Gly Thr Leu Leu Phe Leu Ala Glu Val Val Leu
                180                 185                 190

Leu Cys Trp Val Lys Phe Leu Pro Leu Lys Lys Gln Pro Gly Gln Pro
                195                 200                 205

Arg Pro Thr Ser Lys Pro Pro Ala Ser Gly Ala Ala Ala Val Ser Thr
210                 215                 220

Ser Gly Ile Thr Pro Gly Gln Ala Ala Ala Ile Ala Ser Thr Thr Ile
225                 230                 235                 240

Met Val Pro Phe Gly Leu Ile Phe Ile Val Phe Ala Val His Phe Tyr
                245                 250                 255

Arg Ser Leu Val Ser His Lys Thr Asp Arg Gln Phe Gln Glu Leu Asn
                260                 265                 270

Glu Leu Ala Glu Phe Ala Arg Leu Gln Asp Gln Leu Asp His Arg Gly
                275                 280                 285

Asp His Pro Leu Leu Thr Pro Gly Ser His Tyr
                290                 295
```

CHEMICAL MODULATORS OF STORE-OPERATED CALCIUM CHANNELS AND THEIR THERAPEUTIC APPLICATIONS

CROSS-REFERENCE TO RELATED APPLICATION

This application is a divisional of U.S. patent application Ser. No. 16/141,656, filed Sep. 25, 2018, the disclosure of which is incorporated herein by reference in its entirety.

STATEMENT OF GOVERNMENT LICENSE RIGHTS

This invention was made with Government support under Contract No. R01GM112003 awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is TAMUS167344 SEQ final 2018-09-20.txt. The text file is 2.88 KB; was created on Sep. 20, 2018; and is being submitted via EFS-Web with the filing of the specification.

BACKGROUND OF THE INVENTION

In cells, calcium ($Ca^{2+}$) is an important secondary messenger, and the increase of calcium in cytoplasm is involved in various signaling pathways, further mediating a series of fundamental biological processes, such as contraction of skeletal muscles, release of neurotransmitters, metabolism of mitochondria, gene transcription, cell proliferation, differentiation, and apoptosis. Under normal physiological conditions, cells are exposed to high levels of calcium, and the extracellular concentration of calcium is about 1-2 mM. However, in the cytoplasm, the intracellular calcium concentration is 1,000-10,000 times lower, about $10^{-6}$-$10^{-7}$ M. Additionally, in the intracellular calcium stores, mainly endoplasmic reticulum and sarcoplasmic reticulum, calcium concentration is about $10^{-5}$ M. This calcium gradient constitutes the foundation of calcium serving as a secondary messenger. Aberrant $Ca^{2+}$ signaling is implicated in tumorigenesis and the pathogenesis of immunodeficiency, allergy, and autoimmune and inflammatory disorders. Targeting $Ca^{2+}$ signaling pathway may hold therapeutic potential in the treatment of hematological malignancies and other solid cancers Calcium signal is well controlled through various types of calcium channels in the cell membrane. In excitable cells, such as skeletal muscle and neuronal cells, calcium level is mainly regulated by voltage-gated calcium channels. However, in non-excitable cells, such as lymphocytes and most cancer cells, store-operated calcium (SOC) channel is the major calcium entry pathway from the extracellular space, in which depletion of calcium in intracellular stores can induce calcium influx through cell membrane. To date, several distinct store-operated channels have been reported, with the calcium release-activated calcium (CRAC) channel being the most well-characterized among them.

CRAC channel was first discovered in immune cells, where its function is well studied. Its two key components, the regulatory protein, STIM1 (the stromal interaction molecule 1) and the pore-forming subunit, Orai1 (also known as CRACM1) constitute the molecular basis of the CRAC current. STIM1, a single-transmembrane protein located in endoplasmic reticulum (ER) membrane, can sense the calcium concentration changes in ER. Orai1 has four transmembrane domains and exits as a multimer. After activation by STIM1, Orai1 forms a functional oligomer (most probably as a hexamer) to allow the calcium to pass through the channel. When antigens bind to T-cell and B-cell receptors or when antigen-antibody complex binds to Fc receptors on mast cells, natural killer cells, macrophages, and dendritic cells, phospholipase C (PLC) is activated and in turn hydrolyzes the phosphatidylinositol 4,5 bisphosphate $PIP_2$ to generate inositol-1,4,5-trisphosphate (IP3), which binds to the ER-resident IP3 receptor and triggers the release of $Ca^{2+}$ from the ER lumen into cytoplasm. The decrease of free $Ca^{2+}$ in ER stores is sensed by STIM1 via its ER-luminal EF-SAM domain that contains a $Ca^{2+}$-binding EF-hand motif. Then, STIM1 forms oligomers and migrates toward ER-PM junctions (puncta), where it engages the ORAI1 $Ca^{2+}$ channels and evokes $Ca^{2+}$ influx. Finally, the resultant sustained elevation of cytosolic $Ca^{2+}$ level activates the $Ca^{2+}$/calmodulin-dependent phosphatase calcineurin and transcription factors, including nuclear factor of activated T cells (NFAT), which translocates from the cytoplasm to the nucleus and thereby regulates gene transcription during lymphocyte activation and differentiation. In addition to immune cells, CRAC channel is widely distributed in other various types of cells and tissues, including brain, lung, liver, kidney, spleen, thymus, lymph nodes, skeletal muscle, heart, bone, teeth, etc. Any effectors, such as ligand binding to some GPCRs receptors and tyrosine kinases receptors, that can stimulate the IP3 generation can also induce store-operated calcium current and further mediate the downstream signal pathway and regulated gene transcription.

Although both ORAI and STIM are widely expressed in different tissues, the clinical consequences of dysfunction of CRAC channel are primarily limited to the immune system. Thus, drug candidates that specifically target CRAC channels have a great potential to selectively suppress abnormal immune function and/or reduce the side effects of the existing immunosuppressant drugs, such as cyclosporin and tacrolimus. Additionally, abnormal CRAC channel activity, mainly due to augmented SOCE which resulted in cell calcium overload, was linked with other human diseases, such as myopathy, occlusive vascular diseases, cardiac hypertrophy, pancreatitis, and endothelial dysfunction. The role of CRAC channel in progression of cancers, such as in cancer cell growth, migration, invasion, and metastasis, is beginning to receive more attention. Dysregulated $Ca^{2+}$ influx due to augmented STIM-ORAI signaling has been observed in many types of tumor cells, including breast, prostate, liver, lung, colon, skeletal muscle, cervical, nasopharyngeal, epidermoid, and glioma cancer cells, thereby making CRAC channel an attractive target for drug development.

A number of CRAC channel inhibitors have been developed, such as SKF-96365, 2-APB, BTP. However, presently, there are no viable clinical candidates because of the low selectivity and/or low activity exhibited by these compounds. Therefore, there is still an urgent need and high interest in developing novel CRAC channel inhibitors having high selectivity and potency.

SUMMARY OF THE INVENTION

In one aspect, provided herein is a CRAC channel inhibitor represented by Formula I:

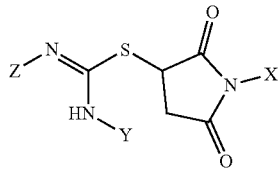

(I)

or a pharmaceutically acceptable salt, solvate, or a hydrate thereof, wherein:

X is an optionally substituted C6-C10 aryl or an optionally substituted C5-C10 heteroaryl;

Y is an optionally substituted C1-C8 alkyl, an optionally substituted C6-C10 aryl-C1-C8 alkyl, an optionally substituted C5-C10 heteroaryl-C1-C8 alkyl, an optionally substituted C3-C10 heteroalkyl, an optionally substituted C3-C6 heterocyclyl, an optionally substituted C6-C10 aryl, or an optionally substituted C5-C10 heteroaryl; and Z is an optionally substituted C6-C10 aryl or an optionally substituted C5-C10 heteroaryl.

In some embodiments of Formula I, X is an optionally substituted phenyl. In some embodiments, X is a phenyl substituted with one, two, or three groups selected from C1-C6 alkyl, carboxyl, alkoxycarbonyl, and amido group.

In some embodiments, the CRAC channel inhibitor has the structure of Formula II:

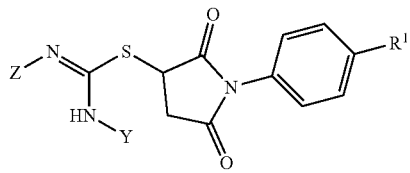

(II)

wherein $R^1$ is H, an optionally substituted C1-C6 alkyl, COOH, $COOR^2$, $CONH_2$, or $CONHR^2$;

$R^2$ is an optionally substituted C1-C6 alkyl;

Y is an optionally substituted C1-C8 alkyl, an optionally substituted C6-C10 aryl-C1-C8 alkyl, or an optionally substituted C5-C10 heteroaryl-C1-C8 alkyl; and Z is an optionally substituted C6-C10 aryl or an optionally substituted C5-C10 heteroaryl.

In some embodiments of Formulae I or II, Y is an optionally substituted phenethyl.

In some embodiments of Formulae I or II, the CRAC channel inhibitor has the structure of Formula III:

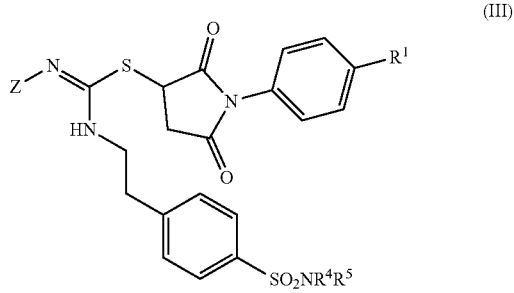

(III)

wherein $R^1$ is H, an optionally substituted C1-C6 alkyl, COOH, $COOR^2$, $CONH_2$, or $CONHR^2$;

$R^2$ is an optionally substituted C1-C6 alkyl;

$R^4$ is H or an optionally substituted C1-C6 alkyl;

$R^5$ is H or an optionally substituted C1-C6 alkyl; and

Z is an optionally substituted C6-C10 aryl or an optionally substituted C5-C10 heteroaryl.

In some embodiments of Formulae I or II, Y is methyl, ethyl, propyl, n-butyl, tert-butyl, cyclopropyl, phenyl, benzyl, 4-methoxybenzyl, 3,4-dimethoxyphenyl, 4-sulfonamidophenethyl, or 5-methylbenzo[d][1,3]dioxolyl.

In some embodiments of Formulae I, II, or III, Z is phenyl, 4-halophenyl, 3-trifluoromethyl-phenyl, 2,5-dichlorophenyl, 3-chloro-4-methyl-phenyl, 2-methoxy-phenyl, 4-methoxy carbonyl-phenyl, benzo[d][1,3]dioxolyl, 3,5-dichlorophenyl, 3-methoxyphenyl, or 3-halophenyl.

In another aspect, provided herein is a method of treatment of a disease, disorder, or condition treatable by inhibiting CRAC channel in a subject, comprising administering to the subject in need thereof an amount of a CRAC channel inhibitor effective to inhibit CRAC channel, wherein the CRAC channel inhibitor is a compound of any one of Formulae I, II, or III.

In some embodiments, the condition treatable by inhibition of CRAC channel activity is an immune system disease, a hyperplastic disease, or cancer. In some embodiments, the condition is colon cancer, breast cancer, leukemia, or glioma. In some embodiments, the condition is an organ or a tissue transplant rejection.

In yet another aspect, provided herein is a pharmaceutical composition comprising a CRAC channel inhibitor represented by Formulae I, II, or III and a pharmaceutically acceptable carrier. In some embodiments, the composition further comprises one or more inactive components such as solvents, excipients, stabilizing agents, or diluents.

In yet another aspect, provided herein is a method of identifying an inhibitor of CRAC channel, the method comprising:
(a) generating on a computer a three-dimensional structure of human Orai1 protein of SEQ ID NO:1 by aligning the sequence of human Orai1 protein with the sequence of Orai1 protein from *Drosophila melanogaster* to generate a homology model of human Orai1;
(b) employing said three-dimensional model from step (a) to identify a potential inhibitor of CRAC;
(c) obtaining said potential inhibitor; and
(d) contacting said potential inhibitor with CRAC to determine the ability of said potential inhibitor to inhibit CRAC activity, whereby inhibition of CRAC activity identifies said inhibitor.

In some embodiments, the potential inhibitor forms hydrophobic or π-π interactions with Trp 377 and Trp 678 amino acids of SEQ ID NO:1 and salt bridge interactions with Arg 384 and Arg 986 amino acids of SEQ ID NO:1.

In some embodiments, the contacting of a potential inhibitor of CRAC with CRAC is an in vitro assay. In some embodiments, the in vitro assay is GFP-NFAT translocation assay.

In yet another aspect, provided herein is a method of preparing a compound of Formula I, wherein the method comprises:

(a) contacting a thiourea compound of Formula IV:

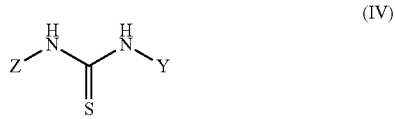

(IV)

with a compound of Formula V:

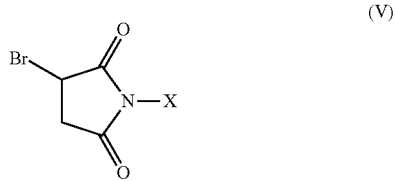

(V)

in a suitable solvent thereby forming the compound of Formula I.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1A:
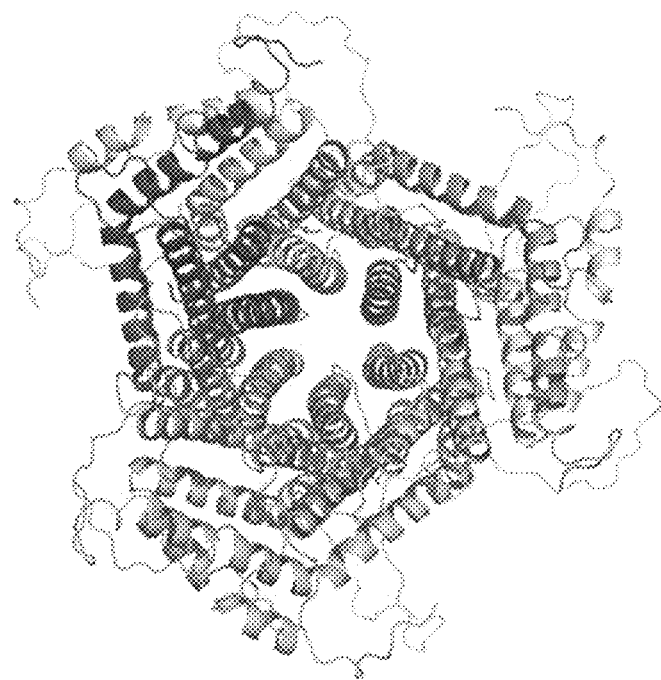
FIGS. 1A and 1B demonstrate the homology model of CRAC channel: top view (2A) and side view (2B).
Figure 1B:
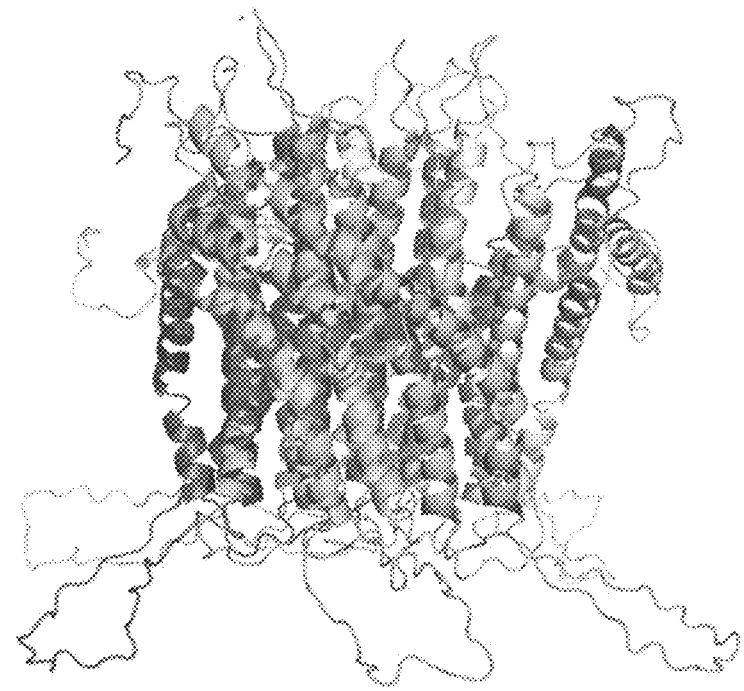

While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Definitions

As used herein, the term "alkyl" includes straight-chain, branched-chain, and cyclic monovalent hydrocarbyl radicals, and combinations thereof, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms, it can be represented as 1-10C, C1-C10, $C_1$-$C_{10}$, $C_{1-10}$, or C1-10. The term "heteroalkyl," as used herein, means the corresponding hydrocarbon wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain plus the number of such heteroatoms that are included as replacements for carbon atoms in the cycle or chain being described.

Alkyl groups can be optionally substituted to the extent that such substitution makes sense chemically. Typical substituents include, but are not limited to, halogens (F, Cl, Br, I), =O, =NCN, =NOR, =NR, OR, $NR_2$, SR, $SO_2R$, $SO_2NR_2$, $NRSO_2R$, $NRCONR_2$, NRC(O)OR, NRC(O)R, CN, C(O)OR, $C(O)NR_2$, OC(O)R, C(O)R, and $NO_2$, wherein each R is independently H, C1-C8 alkyl, C2-C8 heteroalkyl, C1-C8 acyl, C2-C8 heteroacyl, C6-C10 aryl, or C5-C10 heteroaryl, and each R is optionally substituted with halogens (F, Cl, Br, I), =O, =NCN, =NOR', =NR', OR', $NR'_2$, SR', $SO_2R'$, $SO_2NR'_2$, NR'$SO_2R$, NR'CONR'$_2$, NRC(O)OR, NR'C(O)R', CN, C(O)OR', $C(O)NR'_2$, OC(O)R', C(O)R', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl groups can also be substituted by C1-C8 acyl, C2-C8 heteroacyl, C6-C10 aryl, or C5-C10 heteroaryl, each of which can be substituted by the substituents that are appropriate for the particular group.

"Aromatic" or "aryl" substituent or moiety refers to a monocyclic or fused bicyclic moiety having the well-known characteristics of aromaticity; examples of aryls include phenyl and naphthyl. Similarly, "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-14 ring member atoms. Typically, monocyclic heteroaryls contain 5-6 ring members, and bicyclic heteroaryls contain 8-10 ring members. When heteroatoms are allowed to replace carbon atoms in heteroaryl groups, the numbers describing the group, though still written as, e.g. C5-C10, represent the sum of the number of carbon atoms in the cycle plus the number of such heteroatoms that are included as replacements for carbon atoms in the cycle being described. For example, a pyridyl group can be referred to as a C6 heteroaryl.

Aryl and heteroaryl moieties can be substituted with a variety of substituents including C1-C8 alkyl, C5-C12 aryl, C1-C8 acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, $C(O)NR_2$, OC(O)R, C(O)R, and $NO_2$, wherein each R is independently H, C1-C8 alkyl, C2-C8 heteroalkyl, C6-C10 aryl, C5-C10 heteroaryl, C6-C10 aryl-C1-C5 alkyl, or C5-C10 heteroaryl-C1-C5 alkyl, and each R is optionally substituted as described above for alkyl groups. The substituent groups on an aryl or heteroaryl group can be further substituted with the groups described herein as suitable for each type of such substituents or for each component of the substituent. Thus, for example, an arylalkyl substituent can be substituted on the aryl portion with substituents described herein as typical for aryl groups, and it can be further substituted on the alkyl portion with substituents described herein as typical or suitable for alkyl groups.

As used herein, the term "arylalkyl" refers to an alkyl substituted with an aryl. Arylalkyls are represented by the number of carbon atoms in each alkyl and aryl; for example, a C6 aryl-C2 alkyl refers to a C2 alkyl substituted with a C6 aryl. Non-limiting examples of arylalkyls are benzyl (a C6 aryl-C1 alkyl) and phenethyl (a C6 aryl-C2 alkyl). Similarly, the term "heteroarylalkyl" refers to an alkyl substituted with a heteroaryl. Heteroarylalkyls are represented by the number of carbon atoms in each alkyl and heteroaryl; for example, a C6 heteroaryl-C2 alkyl refers to a C2 alkyl, e.g., ethyl, substituted with a C6 heteroaryl, e.g., pyridyl.

"Optionally substituted," as used herein, indicates that the particular group being described can have one or more hydrogen substituents replaced by a non-hydrogen substituent. In some optionally substituted groups or moieties, all hydrogen substituents are replaced by a non-hydrogen substituent (e.g., a polyfluorinated alkyl such as trifluoromethyl). If not otherwise specified, the total number of such substituents that can be present is equal to the number of H atoms present on the unsubstituted form of the group being described. Where an optional substituent is attached via a double bond, such as a carbonyl oxygen or oxo (=O), the group takes up two available valences, so the total number of substituents that may be included is reduced according to the number of available valences.

As used herein, the term "immune system diseases" refers to a series of disorders of the immune system, including immunodeficiency disorders, overactive immune response (allergy), and autoimmune disorders (e.g., disorders in which the immune system attacks normal and healthy tissues). The immune diseases that can be treated with the compounds of the invention are preferably the conditions induced by the overactive or abnormal immune recognition.

A "therapeutically effective amount" refers to an amount effective, at dosages and for periods of time necessary, to achieve the desired therapeutic result, for example, reduced levels of CRAC channel activity. A therapeutically effective amount of a compound can vary according to factors such as the disease state, age, sex, and weight of the subject, and the ability of the compound to elicit a desired response in the subject. An individual therapeutically effective amount can be determined according to the methods known in the art. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of CRAC channel.

As used herein, the term "treat", "treating", and "treatment" refer to administering a compound of the invention or a pharmaceutical composition comprising a compound of the invention to a patient thereby generating a therapeutic effect, such as eliminating or alleviating one or more existing symptoms of a disease, preventing any additional symptoms, and/or preventing further progression of the disease. As used herein, the term "disease, disorder, or condition treatable by inhibiting CRAC channel" refers to a disease, disorder, or condition in which CRAC channel is involved in the pathway related to for the disease, disorder, or condition, and that inhibiting CRAC channel results in the treatment or prevention of the disease, disorder, or condition.

As used herein, the term "transplantation" refers to removal of organs, bone marrow, stem cell, or other tissues from one subject and insertion into another subject. After transplantation, the functionality and viability of the transplanted organs, bone marrow, stem cell, and/or tissues in the new host can be maintained through the use of an immunosuppressant.

Compound Virtual Screening

Figure 2:
FIG. 2 depicts the docking conformations (grey lines) of the compounds in the binding site of the CRAC homology model.
Figure 3:
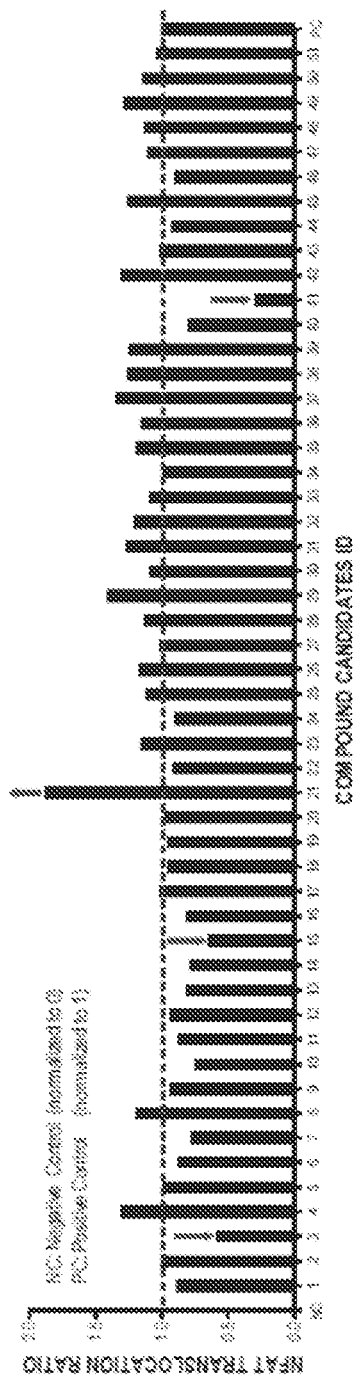
FIG. 3 summarizes the primary activity (NFAT nucleus-to-cytosol ratio) of Compounds 1-51 from the virtual screening.

Compared with the classical drug discovery methods, computer-aided drug discovery is a convenient and low-cost way to find a lead compound with a novel chemical scaffold. To date, few literature reports describing the use of this method to discover CRAC channel inhibitors have been published. In this invention, based on the crystal structure of Orai1 from *Drosophila melanogaster*, the inventors have built a virtual screening method to discover novel CRAC channel inhibitors. Specifically, first the human Orai1 amino acid sequence was obtained from Uniprot database (Uniprot ID: Q96D31). Then, the alignment of the amino acid sequence between human Orai1 protein and *Drosophila melanogaster* Orai1 protein was conducted using the Cobalt method. Then, according to the alignment results, Modeler 9.11 software was used to generate the homology model of human Orai1. Then, the rough model was solvated by using the TIP3P water model, subjected to 500-steps of molecular mechanics minimization and molecular dynamics simulations at 300 K for 1.0 ns using the SANDER module in AMBER 8 program to obtain a refined model, as shown in FIG. 2. Then, using this CRAC homology model and DOCK 6 software, a virtual screening of the SPECS database containing about 300,000 compounds was conducted. About 51 compounds were identified for biological evaluation. The structures of the compounds are shown in Table 1, and the docking results are shown in FIG. 3.

TABLE 1

Structures of some representative hits from the virtual screening experiments

| Compound Number | Structure of the compounds | $IC_{50}$ Value |
|---|---|---|
| 01 | | >200 |
| 02 | | >200 |
| 03 | | 143.7 |
| 04 | | >200 |

TABLE 1-continued

Structures of some representative hits from the virtual screening experiments

| Compound Number | Structure of the compounds | IC$_{50}$ Value |
| --- | --- | --- |
| 05 | | >200 |
| 06 | | >200 |
| 07 | | >200 |
| 08 | | >200 |
| 09 | | >200 |
| 10 | | >200 |
| 11 | | >200 |

TABLE 1-continued

Structures of some representative hits from the virtual screening experiments

| Compound Number | Structure of the compounds | IC$_{50}$ Value |
|---|---|---|
| 12 | | >200 |
| 13 | | >200 |
| 14 | | >200 |
| 15 | | 173.6 |
| 16 | | >200 |
| 17 | | >200 |

TABLE 1-continued

Structures of some representative hits from the virtual screening experiments

| Compound Number | Structure of the compounds | IC$_{50}$ Value |
|---|---|---|
| 18 | | >200 |
| 19 | | >200 |
| 20 | | >200 |
| 21 | | 60.3 (agonist) |
| 22 | | >200 |
| 23 | | >200 |
| 24 | | >200 |

TABLE 1-continued

Structures of some representative hits from the virtual screening experiments

| Compound Number | Structure of the compounds | IC$_{50}$ Value |
|---|---|---|
| 25 | | >200 |
| 26 | | >200 |
| 27 | | >200 |
| 28 | | >200 |
| 29 | | >200 |
| 30 | | >200 |
| 31 | | >200 |

TABLE 1-continued

Structures of some representative hits from the virtual screening experiments

| Compound Number | Structure of the compounds | IC$_{50}$ Value |
| --- | --- | --- |
| 32 |  | >200 |
| 33 |  | >200 |
| 34 |  | >200 |
| 35 |  | >200 |
| 36 |  | >200 |
| 37 |  | >200 |
| 38 |  | >200 |
| 39 |  | >200 |

TABLE 1-continued
Structures of some representative hits from the virtual screening experiments
| Compound Number | Structure of the compounds | IC$_{50}$ Value |
|---|---|---|
| 40 | 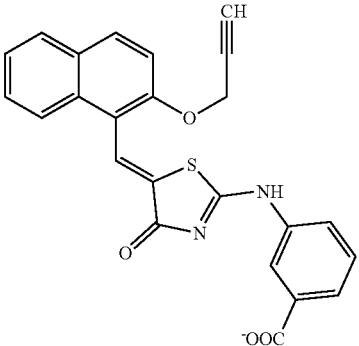 | >200 |
| 41 | 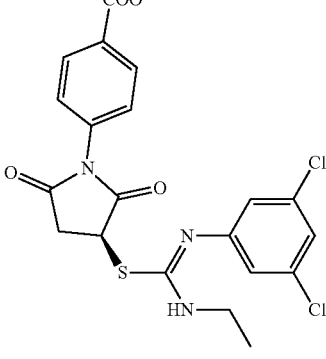 | 278.83 |
| 42 | 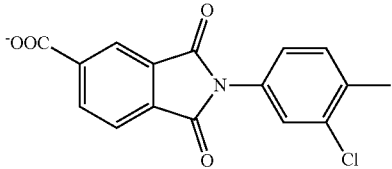 | >200 |
| 43 | 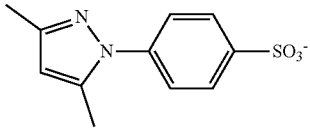 | >200 |
| 44 | 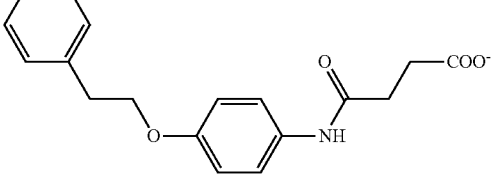 | >200 |
| 45 | 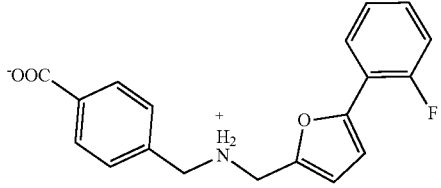 | >200 |

TABLE 1-continued

Structures of some representative hits from the virtual screening experiments

| Compound Number | Structure of the compounds | IC$_{50}$ Value |
|---|---|---|
| 46 | | >200 |
| 47 | | >200 |
| 48 | | >200 |
| 49 | | >200 |
| 50 | | >200 |
| 51 | | >200 |

Inhibitory Activity Assay on CRAC Channel

It is known that thapsigargin (TG) can induce the CRAC channel to open resulting in the calcium influx. The elevation of calcium in cytoplasm can activate the $Ca^{2+}$-calcineurin-NFAT pathway followed by NFAT translocation from the cytoplasm to the nucleus to regulate gene transcription. Therefore, the inventors built a GFP-NFAT translocation-based high-content screening method to evaluate the activity of compounds on CRAC channel. Briefly, a HeLa cell line stably expressing GFP-NFAT was established and used, and the images after chemical stimulation in the presence of TG were acquired using an IN Cell Analyzer 6000 confocal laser imaging system, and then the GFP fluorescent intensity ratio between cytoplasm and nucleus was analyzed to reflect the inhibitory activity of compound on CRAC channel.

Briefly, GFP-NFAT stable cells were cultured in Dulbecco's modified eagle's medium (DMEM) supplemented with 10% FBS in 5% carbon dioxide at 37° C. When it reached 90% confluency, a cell suspension with a concentration of 8000/mL was prepared, and an amount of 2000 cells per well (25 μL/well) was seeded in 384 well plate, putting it at the room temperature for 1 h to make sure the cells distribute evenly, then the cells were incubated overnight. First, primary screening of the selected compounds was conducted. A series of compound solutions with a concentration of 200 μM in MEDM medium were prepared in a 96 well plate and then added to a 384 well plate using a Beckman Coulter automatic drug adding system, in 4 duplicates, and incubated for 30 min at 37° C. SKF was selected as the positive control. Then, 1 μM TG and 1 mM $Ca^{2+}$ were added to 384-well plate using Beckman Coulter automatic drug adding system and incubated for 20 min. Subsequently, 384 well plate was gently washed with PBS twice, and the cells were fixed with 4% PFA (25 μl per well) for 10~15 mins at room temperature, then washed with PBS gently, added 0.5% Triton X-100 (25 μL per well), and incubated for 5 mins aFt room temperature, stained with DAPI (1 μg/mL) for 5~10 mins at room temperature, washed with PBS and added 30 μL PBS per well to image on confocal laser imaging system (objective lens: 10×, FITC and UV). Using Pipeline Plot software (NAFT translocation protocol), the intensity of green fluorescence was analyzed in nucleus and cytosol, calculate the ratio of nucleus:cytosol, normalize TG stimulate NFAT translocation as 1 and no TG adding as 0. Finally, the data was analyzed using GraphPad Prism 5 software. The compounds which showed activity on CRAC channel were further evaluated and the $IC_{50}$ value was calculated using the same method described above.

Figure 4:
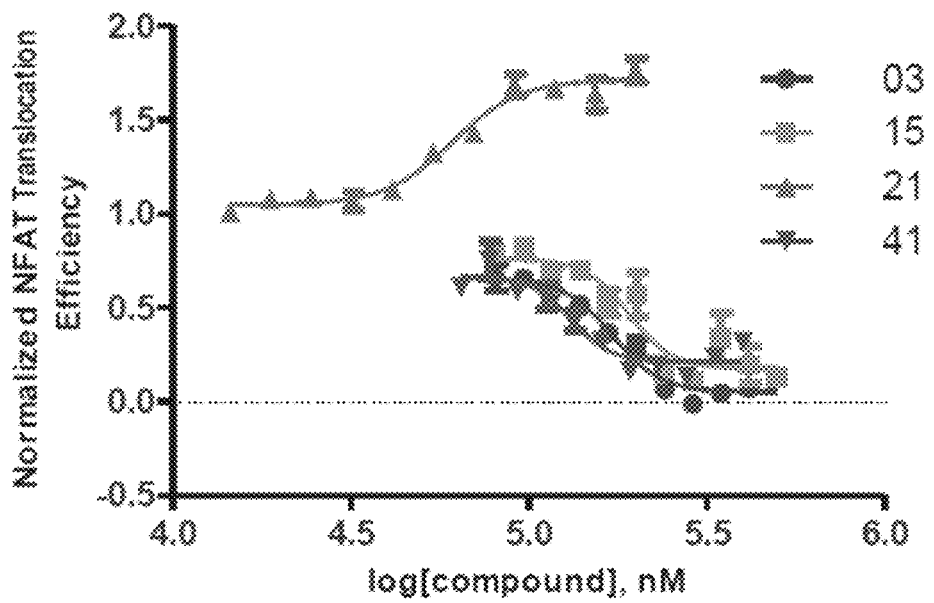
FIG. 4 compares $IC_{50}$ curves of representative Compounds 3, 15, 21, and 41 from the virtual screening.
Figure 5:
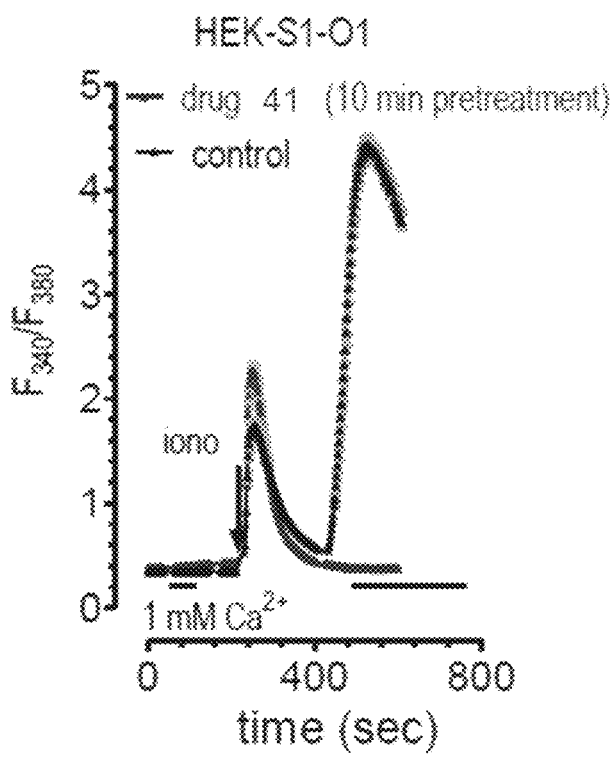
FIG. 5 demonstrates the inhibitory activity of Compound 41, a representative compound, on calcium influx.
Figure 6:
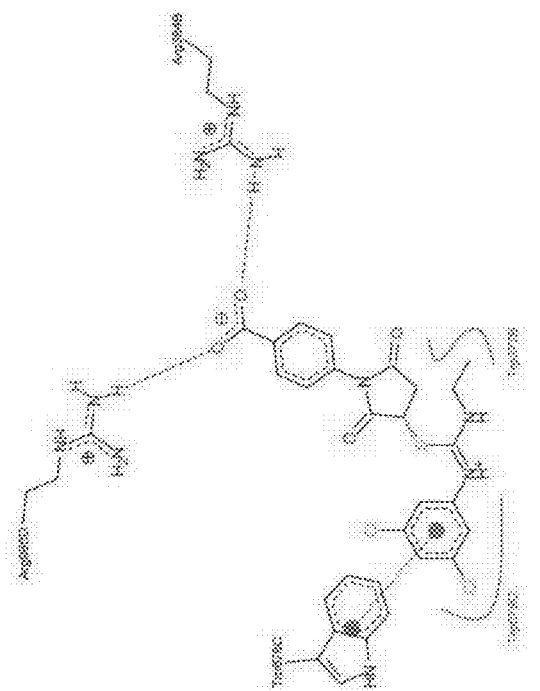
FIG. 6 shows the proposed interactions of Compound 4, a representative compound, with CRAC channel.
Figure 6:
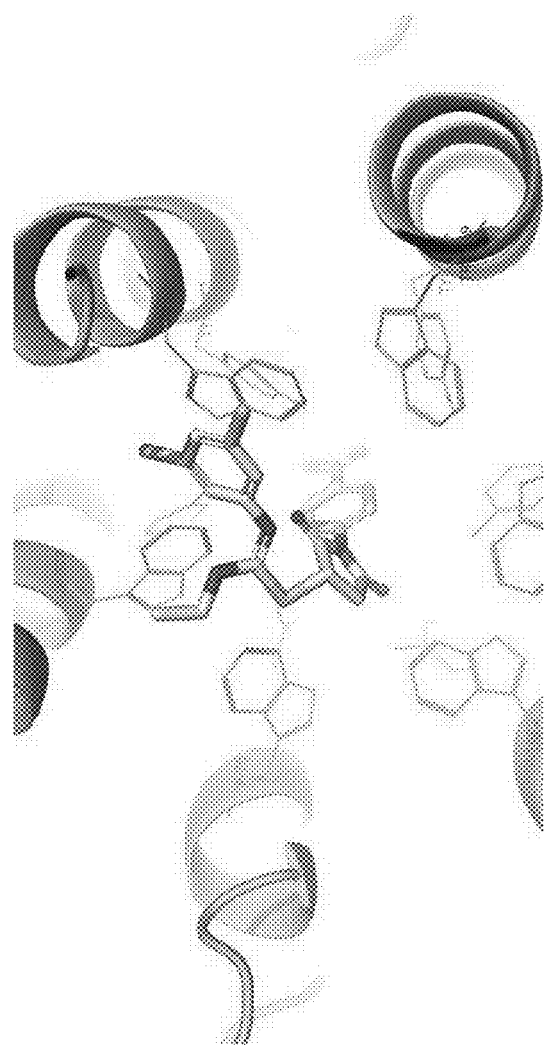

The inhibitor activity on CRAC of these 51 compounds screened out from the small molecule library were evaluated using the method describe above. The result showed that Compounds 03, 15, and 41 demonstrated good activity (FIG. 3). Then, the $IC_{50}$ of these three compounds were calculated, and as shown in FIG. 4, the $IC_{50}$ value was about 100 μM. It was noted that compounds Compound 03 and Compound 41 have a similar chemical structure that contain a general substructure. Therefore, the compounds with the similar chemical structure may have inhibitory activity on calcium influx CRAC channel. In addition, Compound 41 also showed obvious inhibitory activity on calcium influx, as illustrated in FIG. 5. Therefore, the Compound 41 was selected as the lead compound to optimize the structure so as to improve the activity.

Optimization of Compound 41

In order to understand the interaction between Compound 41 and CRAC channel, the structure of Compound 41 was re-docked into the active site, and the interactions were optimized by molecular mechanics and molecular dynamics. After refinements, it was found that the interaction between Compound 41 and CRAC channel seems to be mainly dependent on strong hydrophobic and/or π-π interactions with Trp 377 and Trp 678, as well as salt bridge interactions with Arg 384 and Arg 986 (as shown in FIG. 7).

Figure 7:
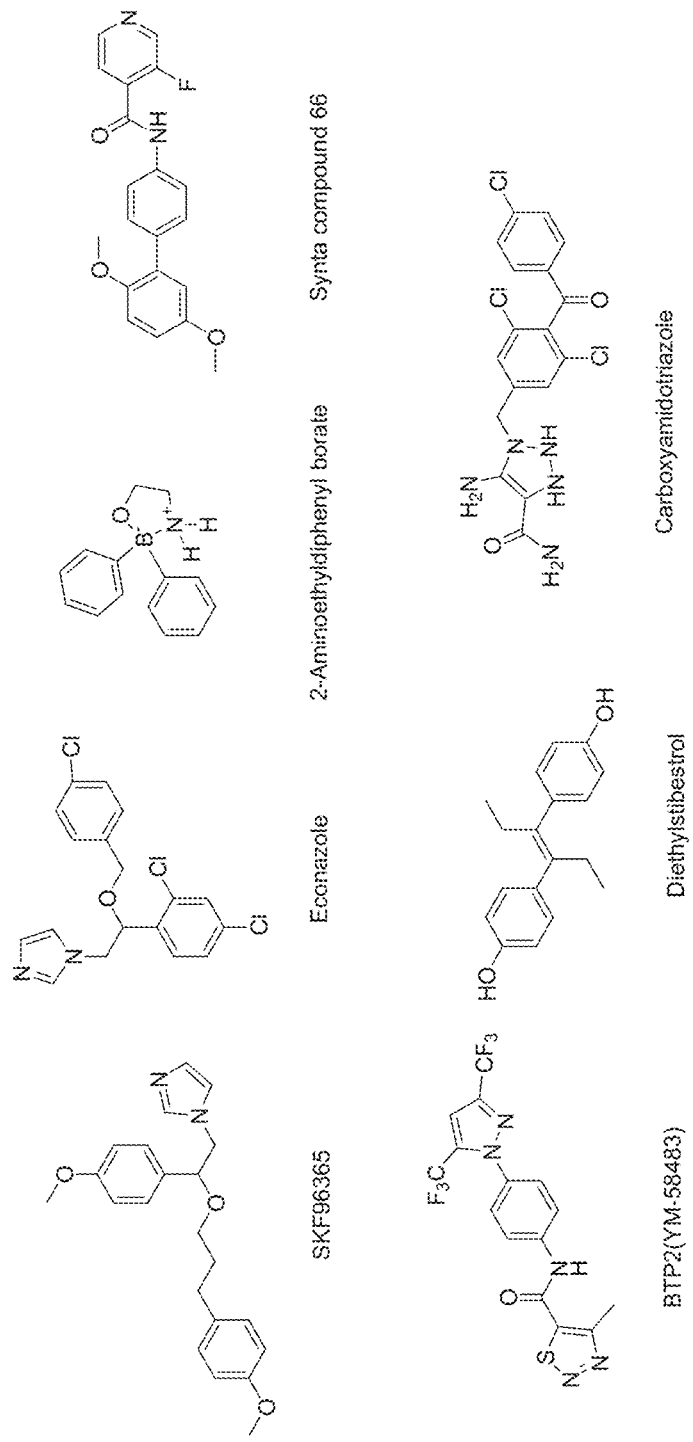
FIG. 7 shows the structure of reported CRAC channel inhibitors that were used as the template to establish the pharmacophores used in the generation of the chemical structures of the compounds of the invention.
Figure 8:
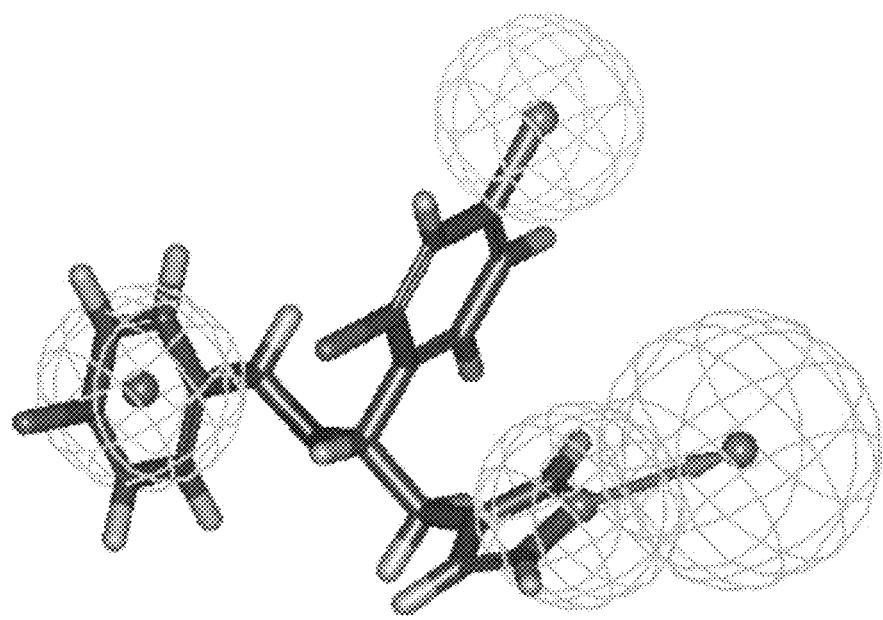
FIG. 8 is the schematic of the pharmacophore model of CRAC inhibitors showing Compound 41, a representative compound, bound to the CRAC channel.
Figure 9A:
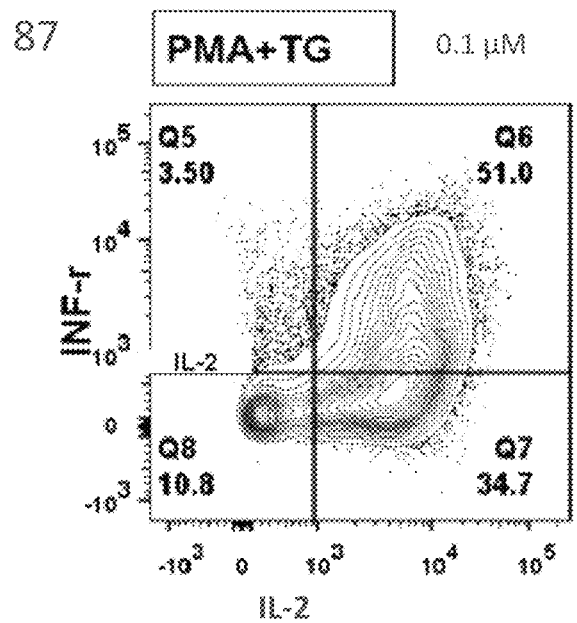
FIGS. 9A-9F demonstrate that representative Compounds 87 (FIGS. 9A, 9C, and 9E) and 53 (FIGS. 9B, 9D, and 9F) significantly inhibit cytokine IL-2 expression in primary T cells, with the calculated $IC_{50}$ of 0.86±0.12 µM and 15.6±1.17 µM, respectively.
Figure 9B:
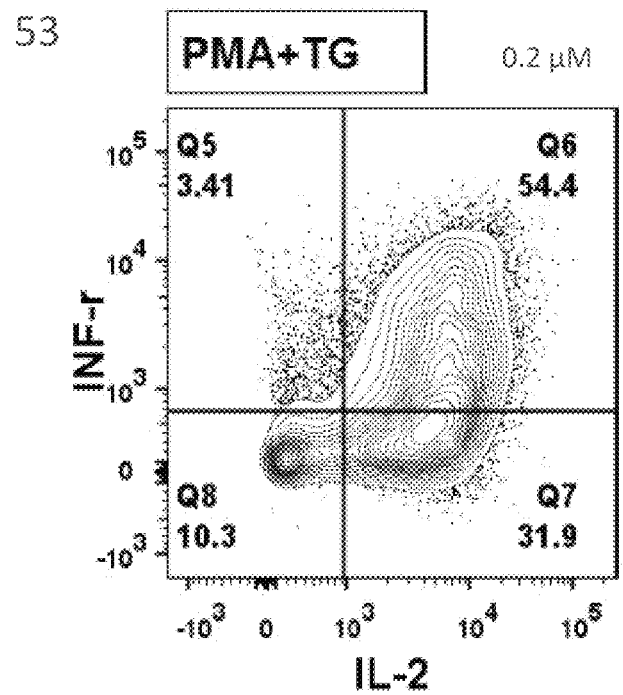
Figure 9C:
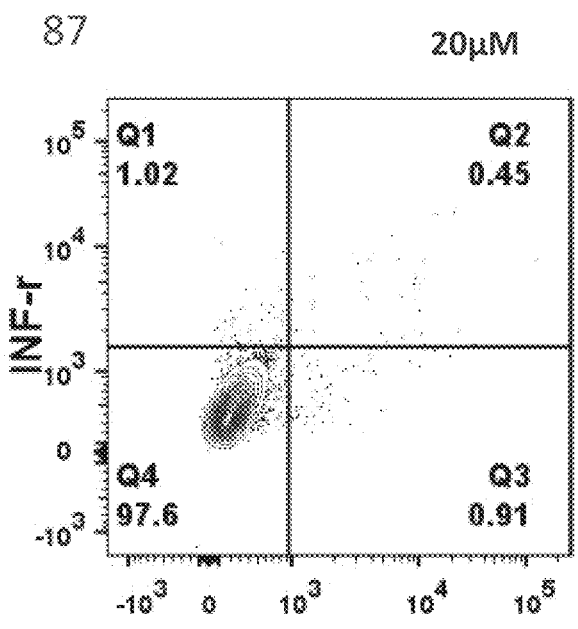
Figure 9D:
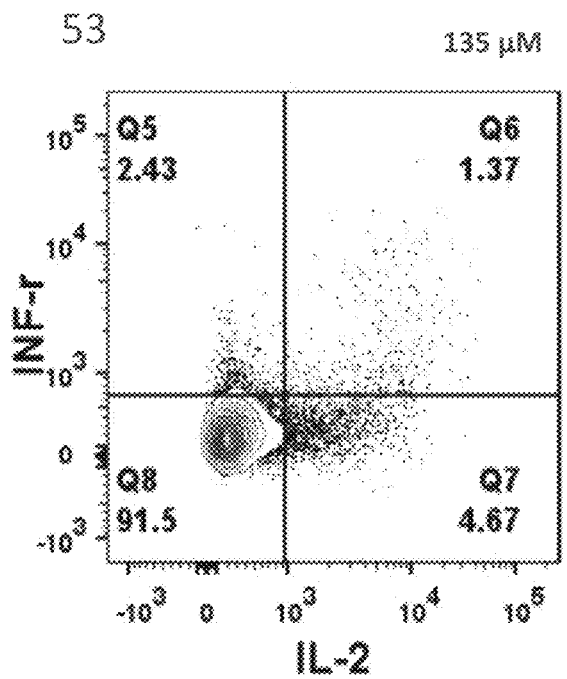
Figure 9E:
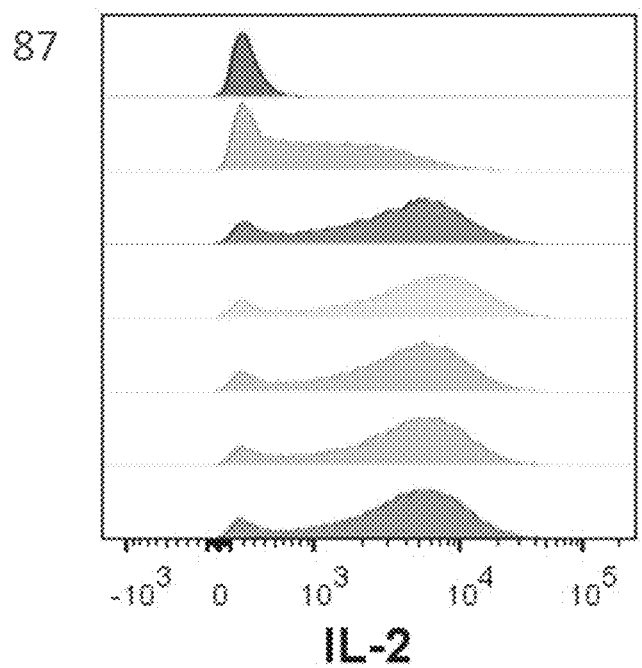
Figure 9F:
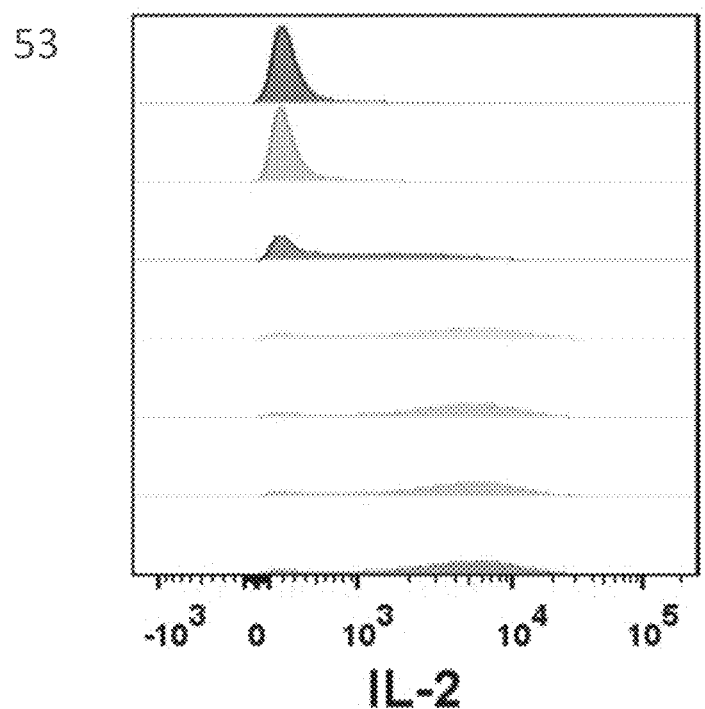

In addition, in order to aid the lead compound optimization, a working pharmacophore model was developed based on the structure of reported CRAC channel inhibitors, which are shown in FIG. 7, using the Hipop algorithm implemented in the Discovery Studio package. Briefly, the initial working pharmacophore model built consisted of three common features as critical fragments for activities: one hydrogen binding acceptor and two hydrophobic groups (as shown in FIG. 8). Such results are consistent with the homology model as well. This model in conjunction with the interaction model was used to guide the optimization of the lead compounds.

Thus, in an aspect, provided herein is a method of identifying an inhibitor of CRAC channel, the method comprising:

(a) generating on a computer a three-dimensional structure of human Orai1 protein of SEQ ID NO:1 by aligning the sequence of human Orai1 protein with the sequence of Orai1 protein from *Drosophila melanogaster* to generate a homology model of human Orai1;

(b) employing said three-dimensional model from step (a) to identify a potential inhibitor of CRAC;

(c) obtaining said potential inhibitor; and (d) contacting said potential inhibitor with CRAC to determine the ability of said potential inhibitor to inhibit CRAC activity, whereby inhibition of CRAC activity identifies said inhibitor.

In some embodiments, the potential inhibitor forms hydrophobic or π-π interactions with Trp 377 and Trp 678 amino acids of SEQ ID NO:1 and salt bridge interactions with Arg 384 and Arg 986 amino acids of SEQ ID NO:1.

In some embodiments, the contacting of a potential inhibitor of CRAC with CRAC is an in vitro assay. In some embodiments, the in vitro assay is GFP-NFAT translocation assay.

In some embodiments, in the optimization procedure described above, the 3-mercapto-pyrrolidine-2,5-dione scaffold of Formula I was fixed, and the X, Y, and Z groups in the structure were varied. This is different from the classical SAR optimization method, in which a series of the lead compound analogs is synthesized via complex and time-consuming synthetic procedures. The inventors searched for analogues of Compound 41 in the existing small molecule libraries, including Zinc, Specs, and other libraries. In addition, PubChem searching pool was used for identification of analogous structures. Some selected compounds (Compounds 52-74) are shown in Table 2.

TABLE 2

Exemplary structures of the compounds optimized from the lead Compound 41 and their inhibitory activity on CRAC channel.

| Compound Number | Compound Structure | $IC_{50}$ of the compounds |
|---|---|---|
| 52 | 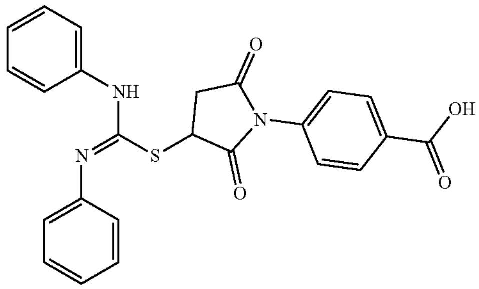 [SMILES: O=C(O)c1ccc(N2C(=O)CC(S/C(=N\c3ccccc3)Nc3ccccc3)C2=O)cc1] | >200 |
| 53 | 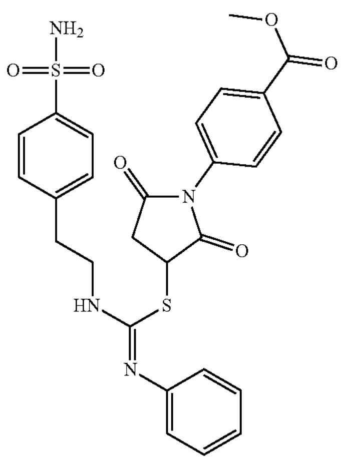 [SMILES: COC(=O)c1ccc(N2C(=O)CC(S/C(=N\c3ccccc3)NCCc3ccc(S(N)(=O)=O)cc3)C2=O)cc1] | 13.0 |
| 54 | 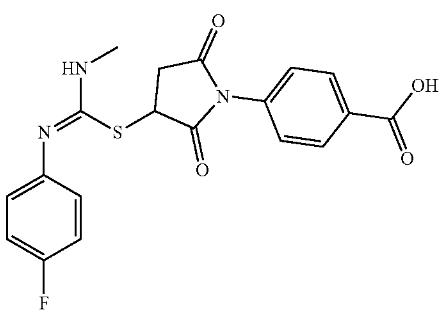 [SMILES: CN/C(=N/c1ccc(F)cc1)SC1CC(=O)N(c2ccc(C(=O)O)cc2)C1=O] | >200 |
| 55 | 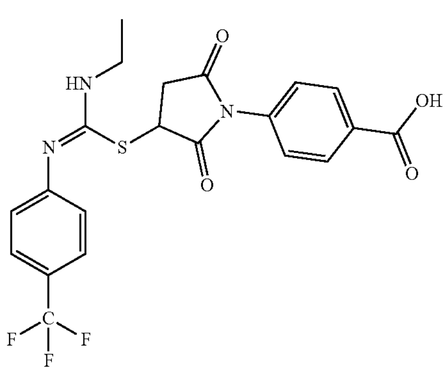 [SMILES: CCN/C(=N/c1ccc(C(F)(F)F)cc1)SC1CC(=O)N(c2ccc(C(=O)O)cc2)C1=O] | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 56 | 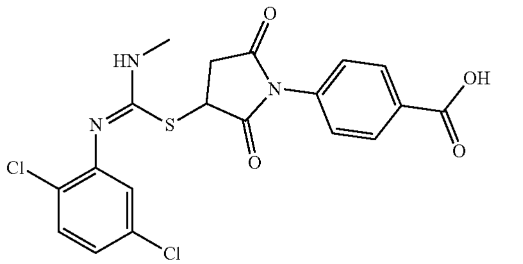 [SMILES: CN/C(=N/c1cc(Cl)ccc1Cl)SC1CC(=O)N(c2ccc(C(=O)O)cc2)C1=O] | >200 |
| 57 | 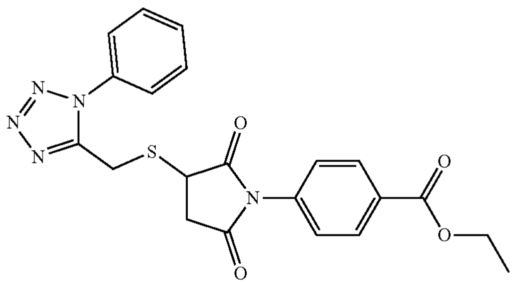 [SMILES: CCOC(=O)c1ccc(N2C(=O)CC(SCc3nnnn3-c3ccccc3)C2=O)cc1] | >200 |
| 58 | 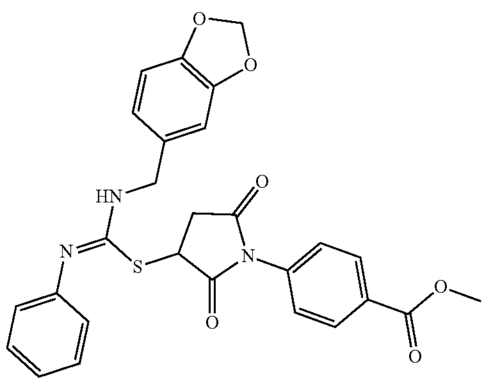 [SMILES: COC(=O)c1ccc(N2C(=O)CC(S/C(=N\c3ccccc3)NCc3ccc4c(c3)OCO4)C2=O)cc1] | >200 |
| 59 | 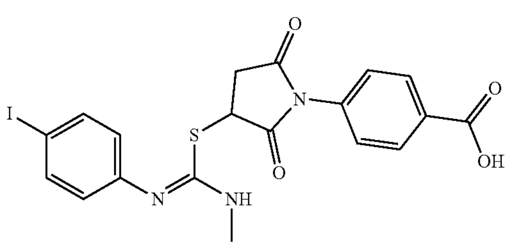 [SMILES: CN/C(=N/c1ccc(I)cc1)SC1CC(=O)N(c2ccc(C(=O)O)cc2)C1=O] | >200 |
| 60 | 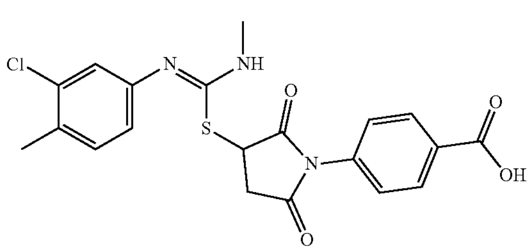 [SMILES: CN/C(=N/c1ccc(C)c(Cl)c1)SC1CC(=O)N(c2ccc(C(=O)O)cc2)C1=O] | >200 |

TABLE 2-continued

Exemplary structures of the compounds optimized from the lead Compound 41 and their inhibitory activity on CRAC channel.

| Compound Number | Compound Structure | $IC_{50}$ of the compounds |
|---|---|---|
| 61 | 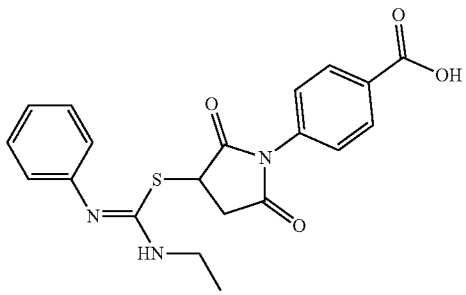 [SMILES: CCN/C(=N/c1ccccc1)SC1CC(=O)N(c2ccc(C(=O)O)cc2)C1=O] | >200 |
| 62 | 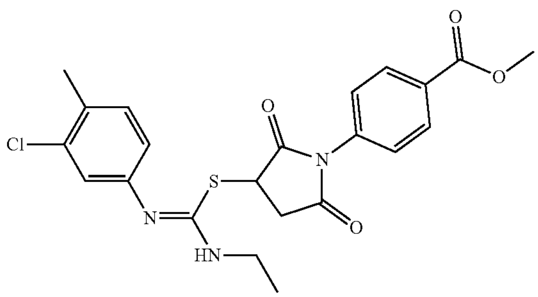 [SMILES: CCN/C(=N/c1ccc(C)c(Cl)c1)SC1CC(=O)N(c2ccc(C(=O)OC)cc2)C1=O] | 11.28 |
| 63 | 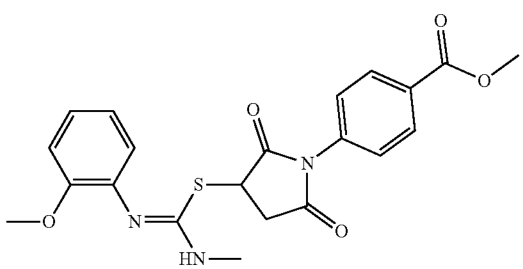 | 74.38 |
| 64 | 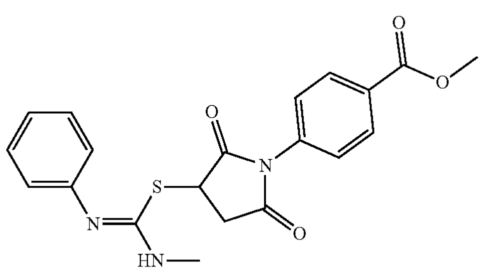 [SMILES: CN/C(=N/c1ccccc1)SC1CC(=O)N(c2ccc(C(=O)OC)cc2)C1=O] | 24.89 |
| 65 | 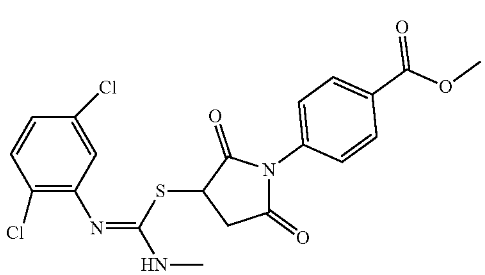 [SMILES: CN/C(=N/c1cc(Cl)ccc1Cl)SC1CC(=O)N(c2ccc(C(=O)OC)cc2)C1=O] | 30.57 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 66 | 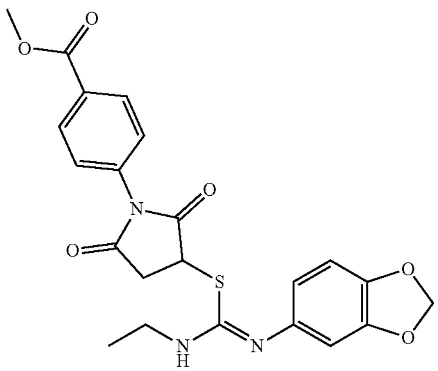 [SMILES: CCN/C(=N/c1ccc2c(c1)OCO2)SC1CC(=O)N(c2ccc(C(=O)OC)cc2)C1=O] | 10.47 |
| 67 | 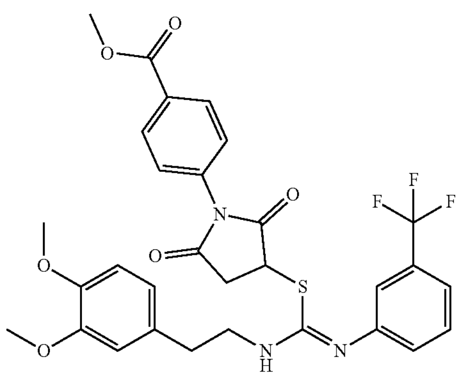 [SMILES: COC(=O)c1ccc(N2C(=O)CC(S/C(=N\c3cccc(C(F)(F)F)c3)NCCc3ccc(OC)c(OC)c3)C2=O)cc1] | >200 |
| 68 | 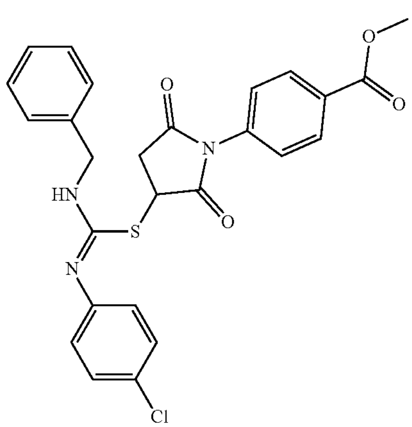 [SMILES: COC(=O)c1ccc(N2C(=O)CC(S/C(=N\c3ccc(Cl)cc3)NCc3ccccc3)C2=O)cc1] | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 69 | 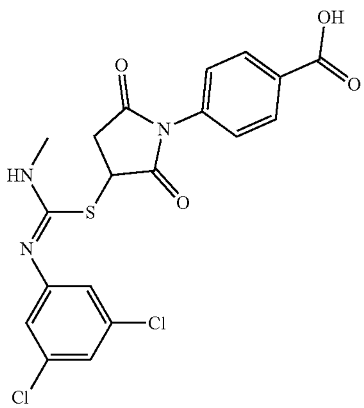 [SMILES: CN/C(=N/c1cc(Cl)cc(Cl)c1)SC1CC(=O)N(c2ccc(C(=O)O)cc2)C1=O] | 107.9 |
| 70 | 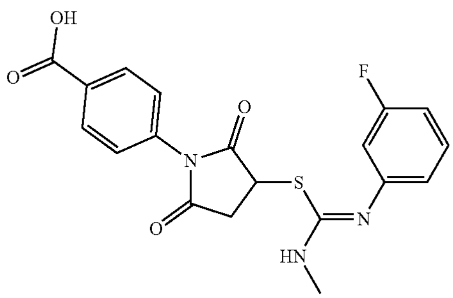 [SMILES: CN/C(=N/c1cccc(F)c1)SC1CC(=O)N(c2ccc(C(=O)O)cc2)C1=O] | >200 |
| 71 | 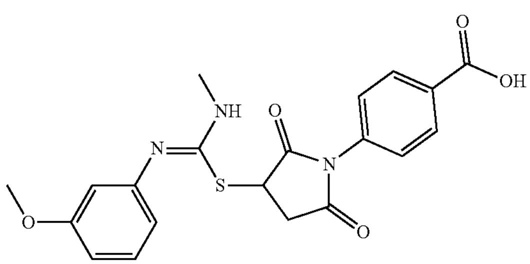 [SMILES: CN/C(=N/c1cccc(OC)c1)SC1CC(=O)N(c2ccc(C(=O)O)cc2)C1=O] | >200 |
| 72 | 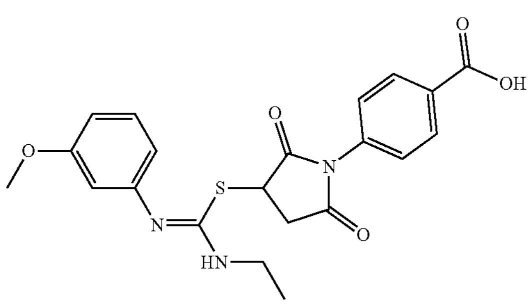 [SMILES: CCN/C(=N/c1cccc(OC)c1)SC1CC(=O)N(c2ccc(C(=O)O)cc2)C1=O] | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 73 | 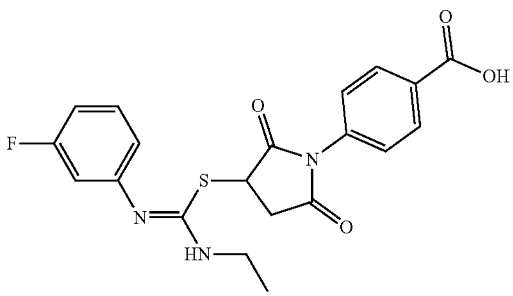 [SMILES: CCN/C(=N/c1cccc(F)c1)SC1CC(=O)N(c2ccc(C(=O)O)cc2)C1=O] | >200 |
| 74 | 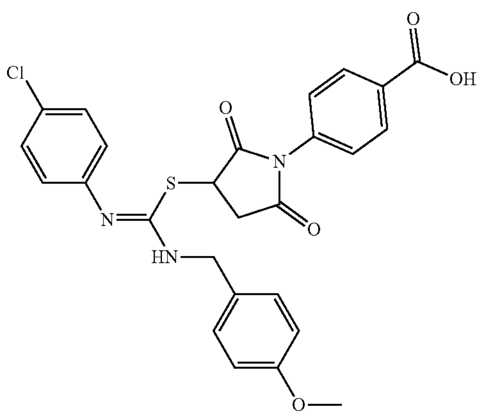 [SMILES: COc1ccc(CN/C(=N/c2ccc(Cl)cc2)SC2CC(=O)N(c3ccc(C(=O)O)cc3)C2=O)cc1] | >200 |
| 75 | 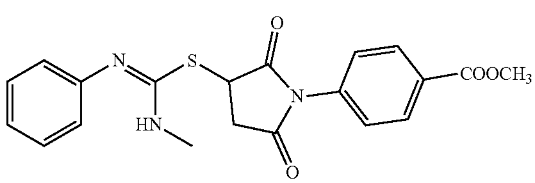 [SMILES: CN/C(=N\c1ccccc1)SC1CC(=O)N(c2ccc(C(=O)OC)cc2)C1=O] | >200 |
| 76 | 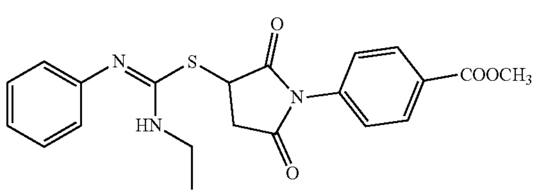 [SMILES: CCN/C(=N\c1ccccc1)SC1CC(=O)N(c2ccc(C(=O)OC)cc2)C1=O] | >200 |
| 77 | 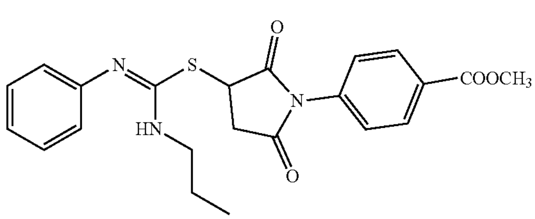 [SMILES: CCCN/C(=N\c1ccccc1)SC1CC(=O)N(c2ccc(C(=O)OC)cc2)C1=O] | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 78 | 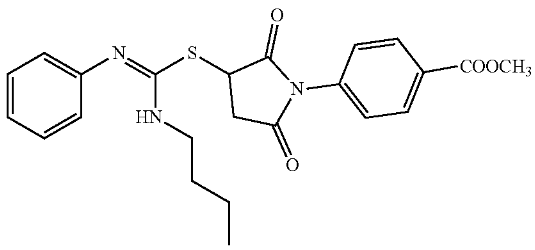 [SMILES: CCCCN/C(=N\c1ccccc1)SC1CC(=O)N(c2ccc(C(=O)OC)cc2)C1=O] | >200 |
| 79 | 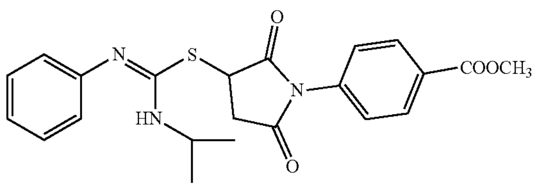 [SMILES: COC(=O)c1ccc(N2C(=O)CC(S/C(=N/c3ccccc3)NC(C)C)C2=O)cc1] | 11.67 |
| 80 | 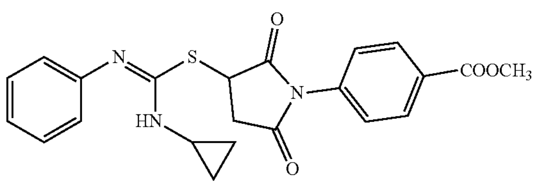 [SMILES: COC(=O)c1ccc(N2C(=O)CC(S/C(=N/c3ccccc3)NC3CC3)C2=O)cc1] | >200 |
| 81 | 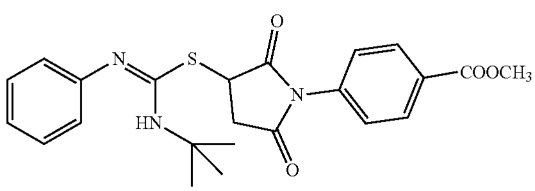 [SMILES: COC(=O)c1ccc(N2C(=O)CC(S/C(=N/c3ccccc3)NC(C)(C)C)C2=O)cc1] | >200 |
| 82 | 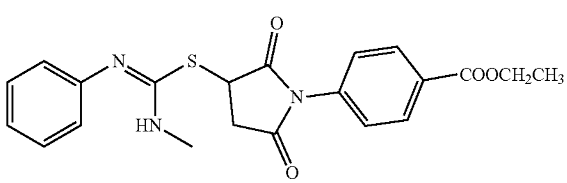 | 22.35 |
| 83 | 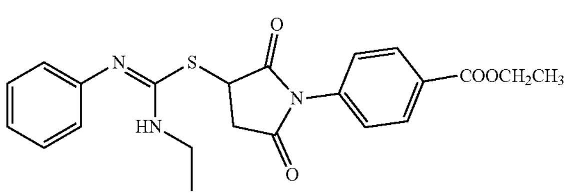 | >200 |
| 84 | 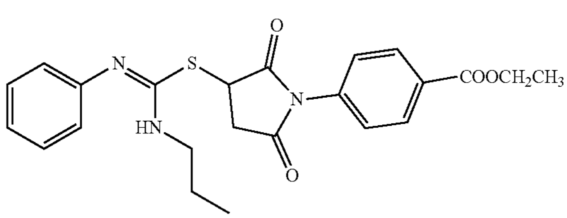 | >200 |

TABLE 2-continued

Exemplary structures of the compounds optimized from the lead Compound 41 and their inhibitory activity on CRAC channel.

| Compound Number | Compound Structure | $IC_{50}$ of the compounds |
|---|---|---|
| 85 | 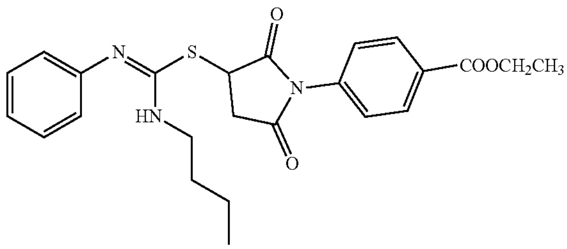 | >200 |
| 86 | 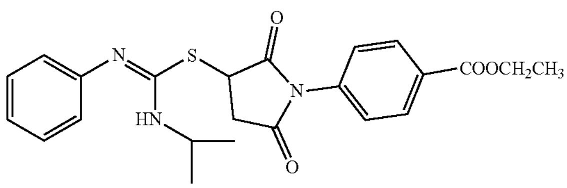 | 6.34 |
| 87 | 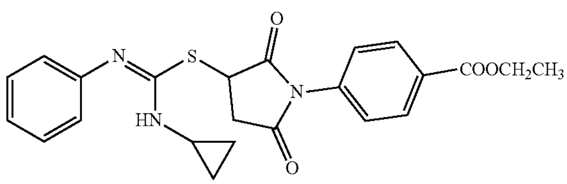 | 0.95 |
| 88 | 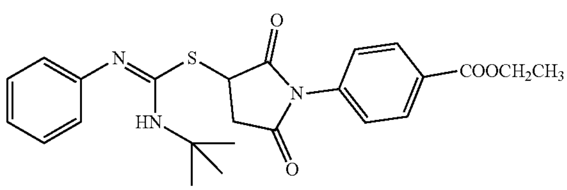 | >200 |
| 89 | 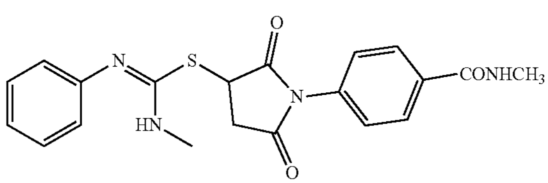 | >200 |
| 90 | 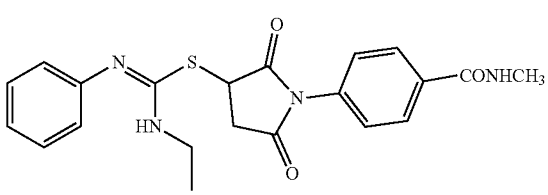 | >200 |
| 91 | 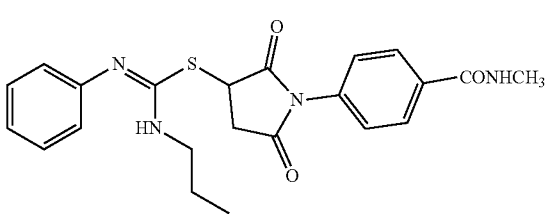 | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 92 | 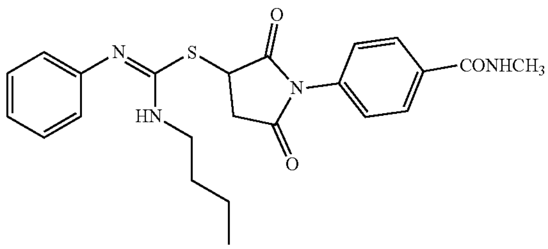 | >200 |
| 93 | 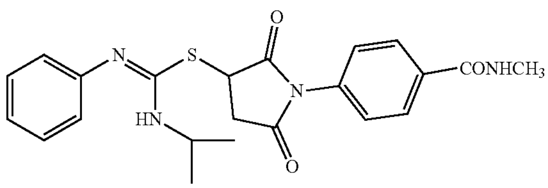 | >200 |
| 94 | 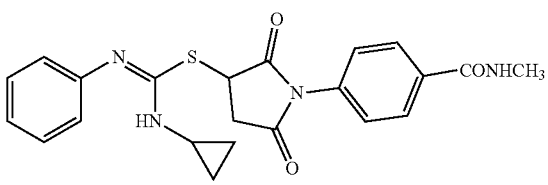 | >200 |
| 95 | 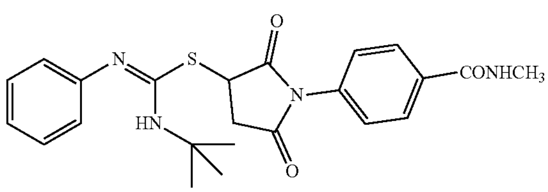 | >200 |
| 96 | 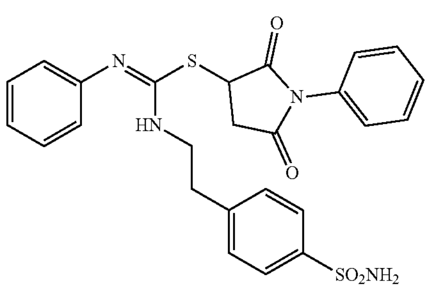 [SMILES: NS(=O)(=O)c1ccc(CCN/C(=N\c2ccccc2)SC2CC(=O)N(c3ccccc3)C2=O)cc1] | 10.89 |
| 97 | 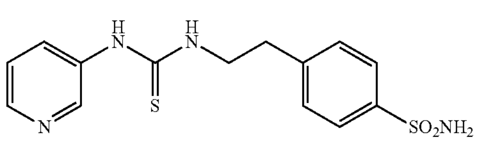 [SMILES: NS(=O)(=O)c1ccc(CCNC(=S)Nc2cccnc2)cc1] | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 98 | 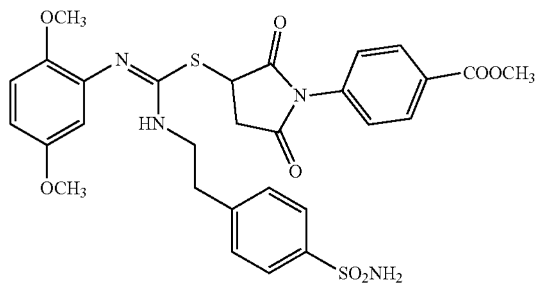 [SMILES: COC(=O)c1ccc(N2C(=O)CC(S/C(=N/c3cc(OC)ccc3OC)NCCc3ccc(S(N)(=O)=O)cc3)C2=O)cc1] | 21.21 |
| 99 | 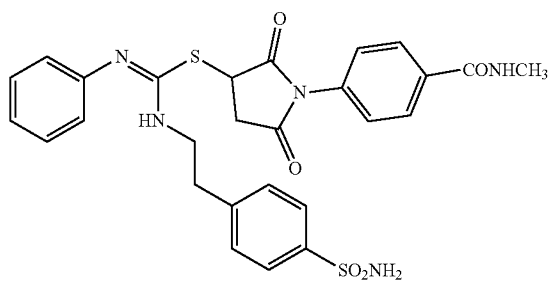 | 18.17 |
| 100 | 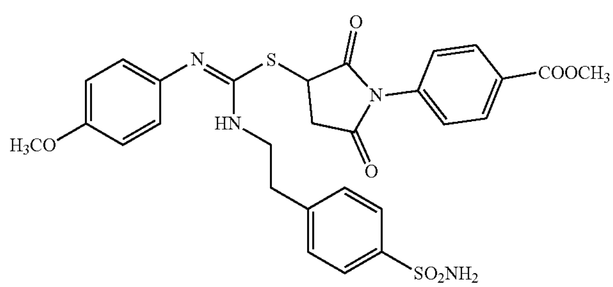 [SMILES: COC(=O)c1ccc(N2C(=O)CC(S/C(=N/c3ccc(OC)cc3)NCCc3ccc(S(N)(=O)=O)cc3)C2=O)cc1] | 14.82 |
| 101 | 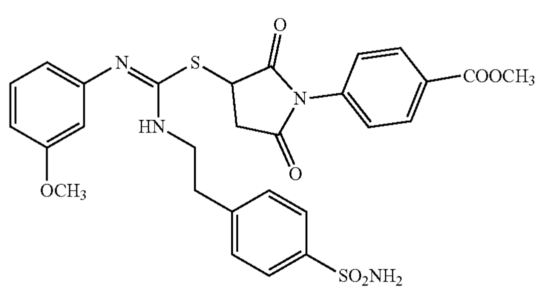 [SMILES: COC(=O)c1ccc(N2C(=O)CC(S/C(=N/c3cccc(OC)c3)NCCc3ccc(S(N)(=O)=O)cc3)C2=O)cc1] | 11.21 |
| 102 | 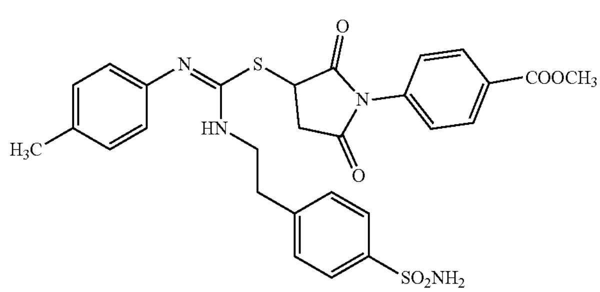 [SMILES: COC(=O)c1ccc(N2C(=O)CC(S/C(=N/c3ccc(C)cc3)NCCc3ccc(S(N)(=O)=O)cc3)C2=O)cc1] | 9.20 |

TABLE 2-continued

Exemplary structures of the compounds optimized from the lead Compound 41 and their inhibitory activity on CRAC channel.

| Compound Number | Compound Structure | $IC_{50}$ of the compounds |
|---|---|---|
| 103 | 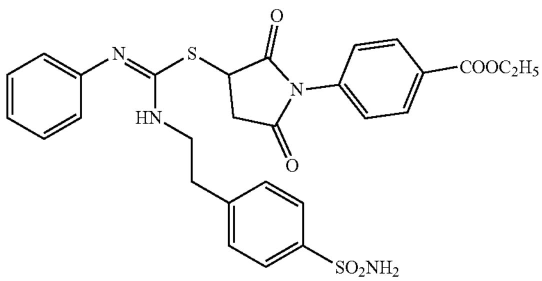 | 15.84 |
| 104 | 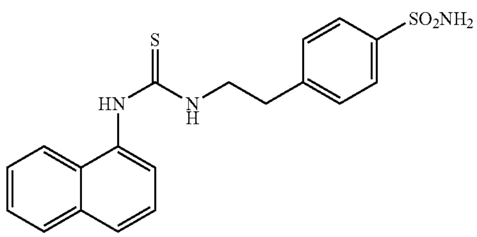 [SMILES: NS(=O)(=O)c1ccc(CCNC(=S)Nc2cccc3ccccc23)cc1] | >200 |
| 105 | 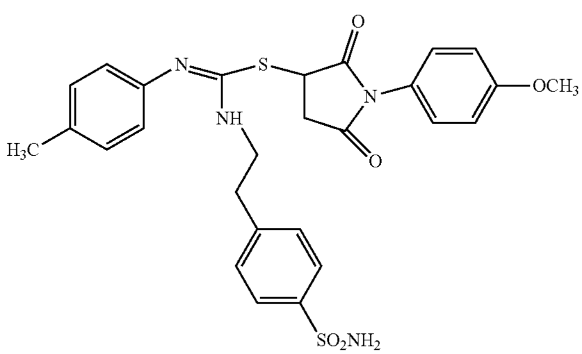 [SMILES: COc1ccc(N2C(=O)CC(S/C(=N/c3ccc(C)cc3)NCCc3ccc(S(N)(=O)=O)cc3)C2=O)cc1] | >200 |
| 106 | 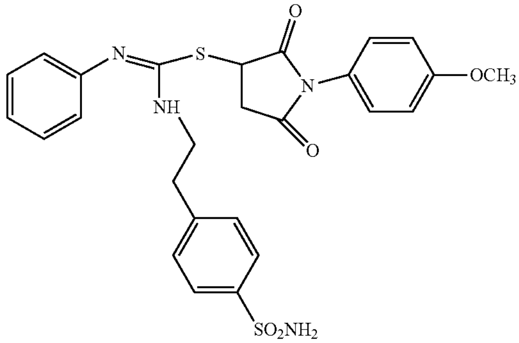 [SMILES: COc1ccc(N2C(=O)CC(S/C(=N/c3ccccc3)NCCc3ccc(S(N)(=O)=O)cc3)C2=O)cc1] | 5.01 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 107 | 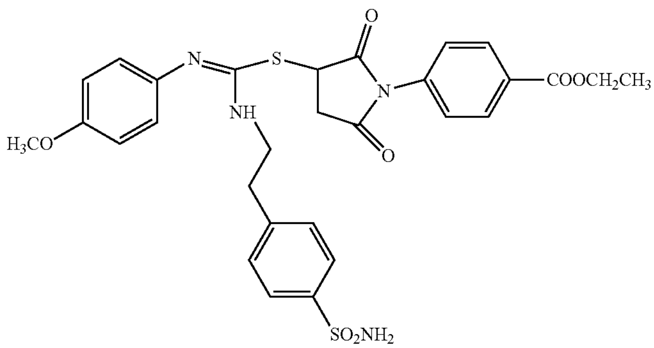 | >200 |
| 108 | 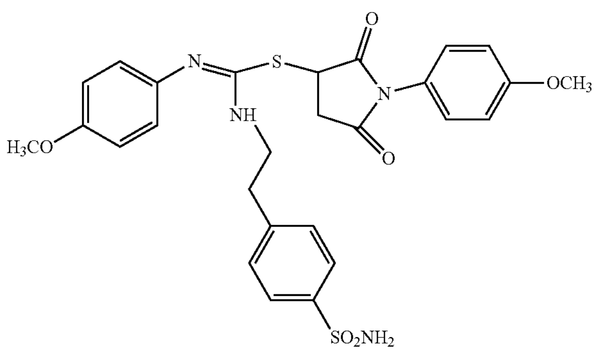 [SMILES: COc1ccc(/N=C(\NCCc2ccc(S(N)(=O)=O)cc2)SC2CC(=O)N(c3ccc(OC)cc3)C2=O)cc1] | >200 |
| 109 | 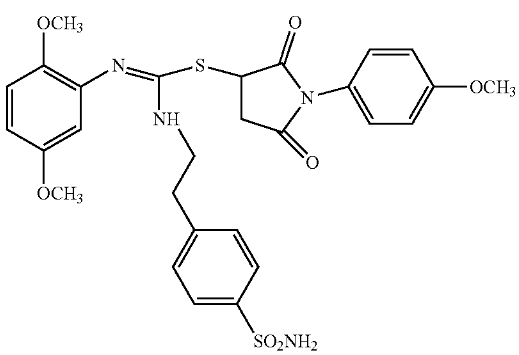 [SMILES: COc1ccc(N2C(=O)CC(S/C(=N/c3cc(OC)ccc3OC)NCCc3ccc(S(N)(=O)=O)cc3)C2=O)cc1] | >200 |
| 110 | 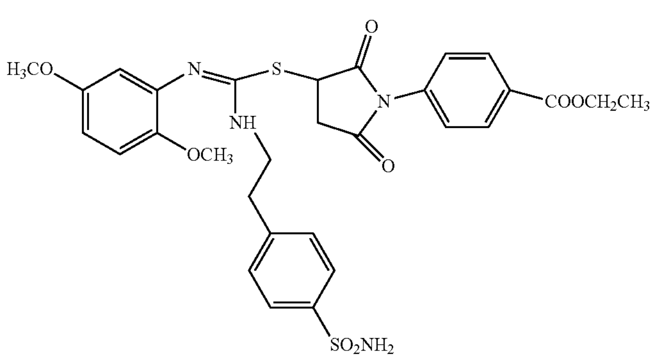 | >200 |

TABLE 2-continued
Exemplary structures of the compounds optimized from the lead Compound 41 and their inhibitory activity on CRAC channel.
| Compound Number | Compound Structure | IC$_{50}$ of the compounds |
|---|---|---|
| 111 | 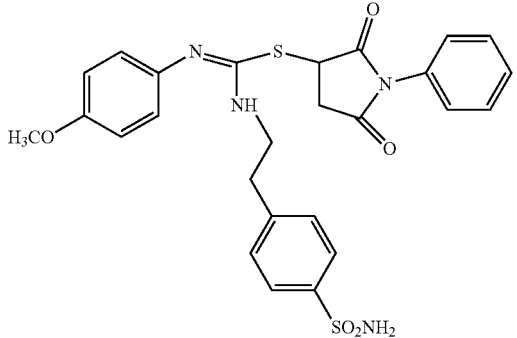 [SMILES: COc1ccc(/N=C(\NCCc2ccc(S(N)(=O)=O)cc2)SC2CC(=O)N(c3ccccc3)C2=O)cc1] | 1.60 |
| 112 | 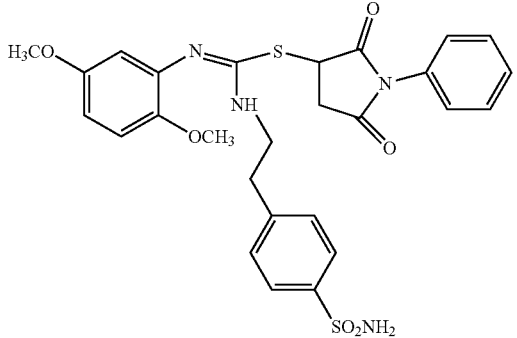 [SMILES: COc1ccc(OC)c(/N=C(\NCCc2ccc(S(N)(=O)=O)cc2)SC2CC(=O)N(c3ccccc3)C2=O)c1] | 0.20 |
| 113 | 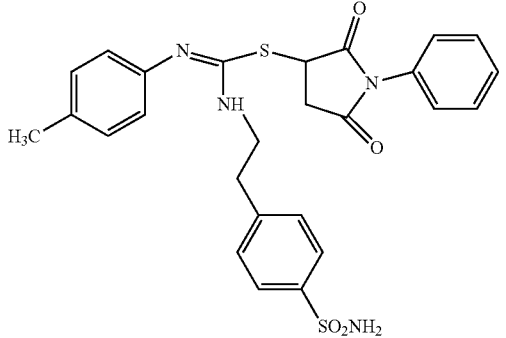 [SMILES: Cc1ccc(/N=C(\NCCc2ccc(S(N)(=O)=O)cc2)SC2CC(=O)N(c3ccccc3)C2=O)cc1] | 5.83 |
| 114 | 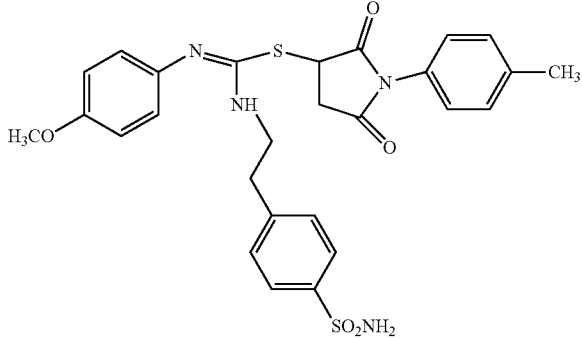 [SMILES: COc1ccc(/N=C(\NCCc2ccc(S(N)(=O)=O)cc2)SC2CC(=O)N(c3ccc(C)cc3)C2=O)cc1] | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 115 | 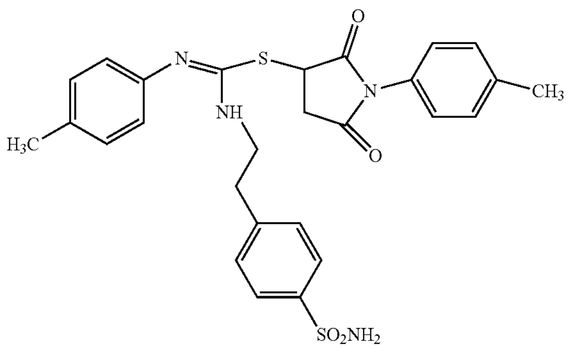 | 5.84 |
| 116 | 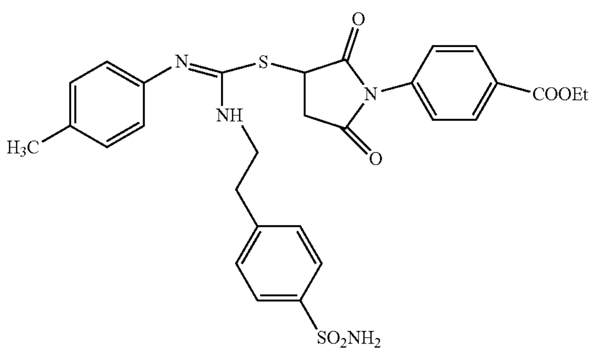 [SMILES: CCOC(=O)c1ccc(N2C(=O)CC(S/C(=N/c3ccc(C)cc3)NCCc3ccc(S(N)(=O)=O)cc3)C2=O)cc1] | >200 |
| 117 | 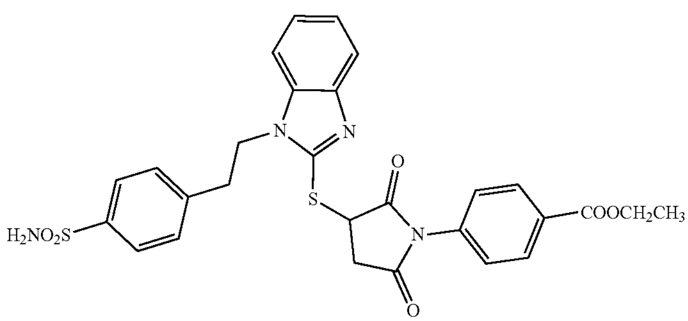 | >200 |
| 118 | 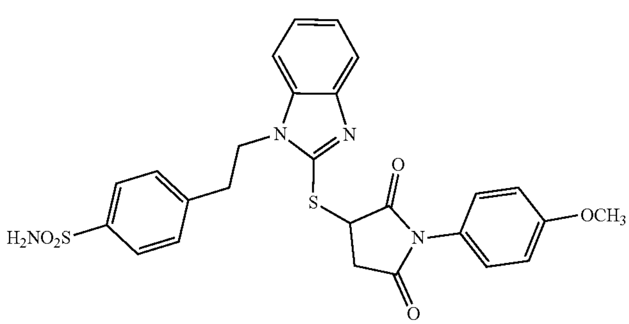 [SMILES: COc1ccc(N2C(=O)CC(Sc3nc4ccccc4n3CCc3ccc(S(N)(=O)=O)cc3)C2=O)cc1] | >200 |

TABLE 2-continued

Exemplary structures of the compounds optimized from the lead Compound 41 and their inhibitory activity on CRAC channel.

| Compound Number | Compound Structure | IC$_{50}$ of the compounds |
|---|---|---|
| 119 | 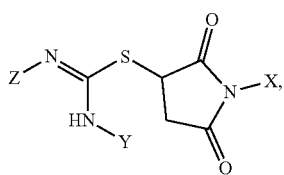 | >200 |
| 120 | 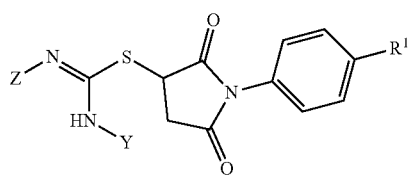 | >200 |

In some embodiments, the CRAC channel inhibitors described herein have the general structure of Formula I:

$$\text{(I)}$$

wherein
X is an optionally substituted alkyl, an optionally substituted heterocyclyl, an optionally substituted aryl, or an optionally substituted heteroaryl;
Y is an optionally substituted alkyl, an optionally substituted heterocyclyl, an optionally substituted aryl, or an optionally substituted heteroaryl; and
Z is an optionally substituted alkyl, an optionally substituted heterocyclyl, an optionally substituted aryl, or an optionally substituted heteroaryl.

In some embodiments of Formula I, X is an optionally substituted C6-C10 aryl or an optionally substituted C5-C10 heteroaryl;
Y is an optionally substituted C1-C8 alkyl, an optionally substituted C6-C10 aryl-C1-C8 alkyl, an optionally substituted C5-C10 heteroaryl-C1-C8 alkyl, an optionally substituted C3-C10 heteroalkyl, an optionally substituted C3-C6 heterocyclyl, an optionally substituted C6-C10 aryl, or an optionally substituted C5-C10 heteroaryl; and
Z is an optionally substituted C6-C10 aryl or an optionally substituted C5-C10 heteroaryl.

In some embodiments of Formula I, X is an optionally substituted phenyl. In some embodiments, X is a phenyl substituted with one or more groups selected from halogen, C1-C6 alkyl, carboxyl, alkoxycarbonyl, amido, or a combination thereof. In some embodiments, X is an unsubstituted phenyl.

In some embodiments of Formula I, X is an optionally substituted C5 or C6 heteroaryl, such as thiophenyl, pyridyl, or pyrimidinyl. In some embodiments of Formula I, X is a C5 or C6 heteroaryl substituted with one or more groups selected from halogen, C1-C6 alkyl, carboxyl, alkoxycarbonyl, amido, or a combination thereof. In some embodiments of Formula I, X is a 4-substituted phenyl, wherein the substituent is an optionally substituted C1-C6 alkyl, COOH, COOR$^2$, CONH$^2$, or CONHR$^2$, wherein R$^2$ is an optionally substituted C1-C6 alkyl In some embodiments, the CRAC channel inhibitors described herein have the structure of Formula II:

$$\text{(II)}$$

wherein
R$^1$ is H, an optionally substituted C1-C6 alkyl, COOH, COOR$^2$, CONH$_2$, or CONHR$^2$;
R$^2$ is an optionally substituted C1-C6 alkyl;
Y is an optionally substituted C1-C8 alkyl, an optionally substituted C6-C10 aryl-C1-C8 alkyl, or an optionally substituted C5-C10 heteroaryl-C1-C8 alkyl; and
Z is an optionally substituted C6-C10 aryl or an optionally substituted C5-C10 heteroaryl.

In some embodiments of Formulae I or II, Y is (CH$_2$)$_n$Ar, wherein n is an integer between 1 and 5 and Ar is an optionally substituted C6-C10 aryl or C5-C10 heteroaryl. In some embodiments, Y is an optionally substituted phenethyl. In some embodiments, Y is a phenethyl substituted with 1 or 2 groups selected from halogen, SO$_2$NHR$^3$, CO$_2$R$^3$, or CONHR$^3$, wherein R$^3$ is H or C1-C6 alkyl.

In some embodiments of Formulae I or II, Y is methyl, ethyl, propyl, n-butyl, tert-butyl, cyclopropyl, phenyl, benzyl, 4-methoxybenzyl, 3,4-dimethoxyphenyl, 4-sulfonamidophenethyl, or 5-methylbenzo[d][1,3]dioxolyl.

In some embodiments, the CRAC channel inhibitors described herein have the structure of Formula III:

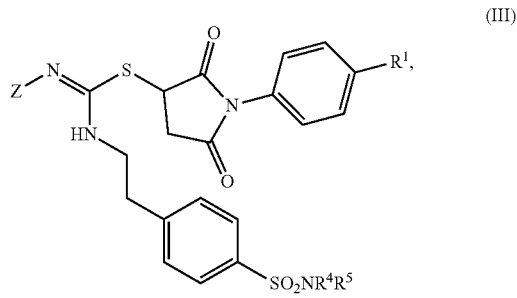

(III)

wherein
$R^1$ is H, an optionally substituted C1-C6 alkyl, COOH, $COOR^2$, $CONH_2$, or $CONHR^2$;
$R^2$ is an optionally substituted C1-C6 alkyl;
$R^4$ is H or an optionally substituted C1-C6 alkyl;
$R^5$ is H or an optionally substituted C1-C6 alkyl; and
Z is an optionally substituted C6-C10 aryl, or an optionally substituted C2-C10 heteroaryl.

In some embodiments of Formulae I, II, or III, Z is phenyl, 4-halophenyl, 3-trifluoromethyl-phenyl, 2,5-dichlorophenyl, 3-chloro-4-methyl-phenyl, 2-methoxyphenyl, 4-methoxycarbonyl-phenyl, benzo[d][1,3]dioxolyl, 3,5-dichlorophenyl, 3-methoxyphenyl, or 3-halophenyl.

In some embodiments of Formula III, $R^4$ and $R^5$ are H.

In some embodiments, the condition treatable by inhibition of CRAC channel activity is an immune system disease, a hyperplastic disease, or cancer. In some embodiments, the condition is colon cancer, breast cancer, leukemia, or glioma. In some embodiments, the condition is an organ or a tissue transplant rejection.

The activity CRAC channel inhibitory activity of the compounds of Formulae I, II, or III disclosed herein can be determined in vitro, for example, using a GFP-NFAT translocation assay method as described below.

Using the GFP-NFAT translocation assay method, the inhibitory activity of the selected compounds at 200 μM concentration was evaluated. As demonstrated in Table 2, several compounds showed good inhibition of CRAC channel, for example, Compounds 53, 62, 65, and 66. Then, $IC_{50}$ values were calculated, with Compound 53 having the lowest $IC_{50}$ at 8.14 μM. This $IC_{50}$ value demonstrates an order of magnitude, e.g., about tenfold, improvement compared to the $IC_{50}$ of the lead Compound 41 (shown in Table 1). Based on the result, a series of Compound 53 analogues was designed and synthesized de novo. The structures of several exemplary synthesized compounds (Compounds 75-104) are shown in Table 2.

The compounds described herein showed good inhibitory activity on CRAC channel. Analyzing the structure and activity relationship, it was found that group Y in Formula I is important for activity. In some embodiments, retaining the 4-sulfonamide-phenethyl group resulted in the preservation of the compound activity. In certain embodiments, if 3-substituted 2,5-pyrrolidinedione core structure was disrupted, the inhibitory activity disappeared.

Pharmaceutical Application of Compounds

Figure 10:
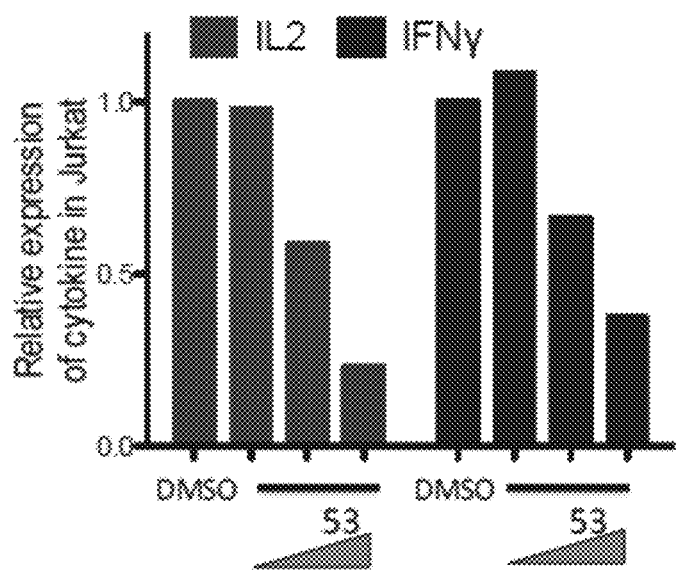
FIG. 10 shows that Compound 53 inhibits cytokine expression in Jurkat cells.
Figure 11A:
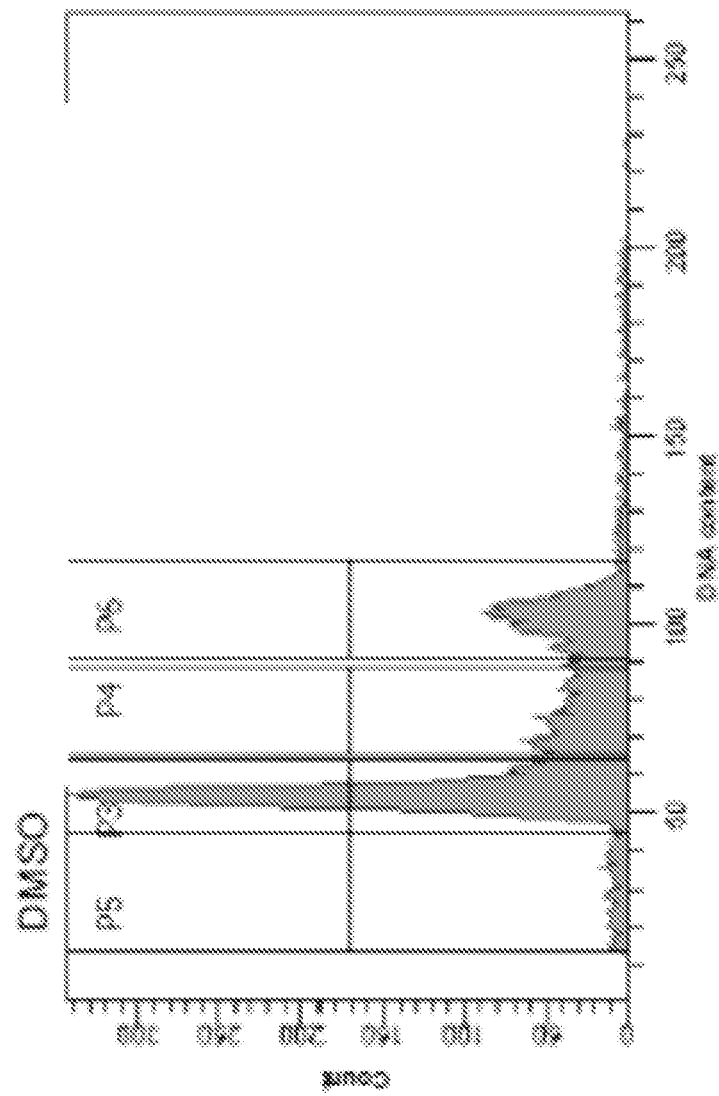
FIGS. 11A and 11B demonstrate the effect of Compound 87 on cell cycle in Jurkat cells: control (11A), Compound 87 (11B).
Figure 11B:
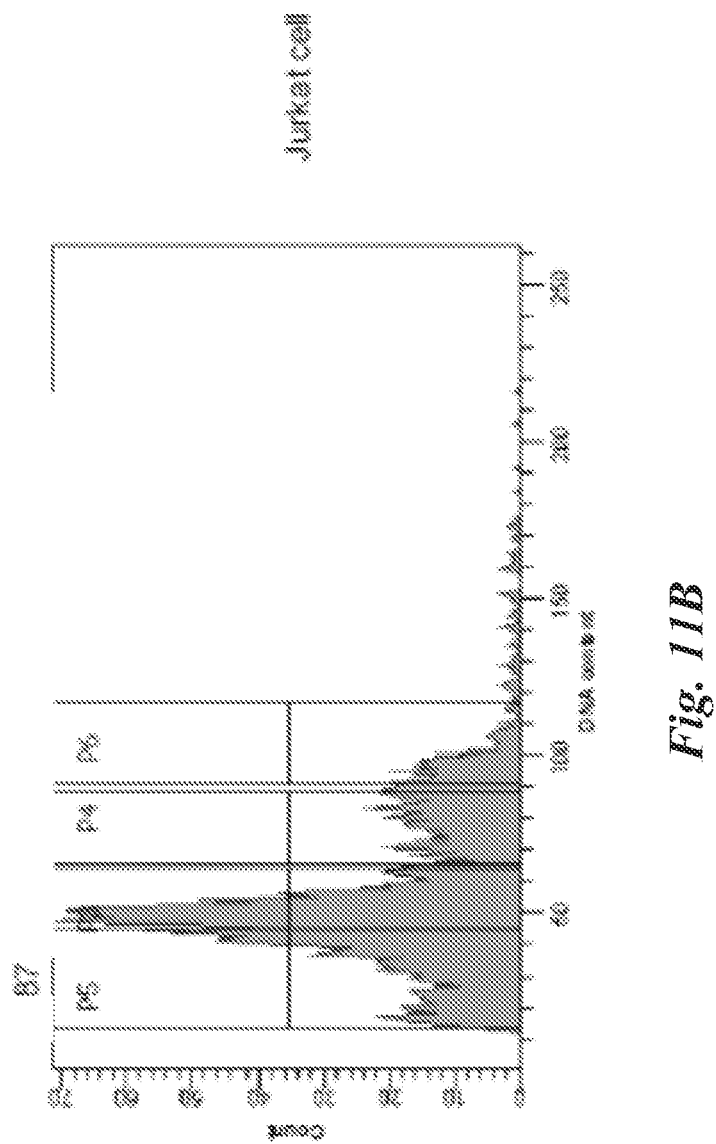
Figure 12A:
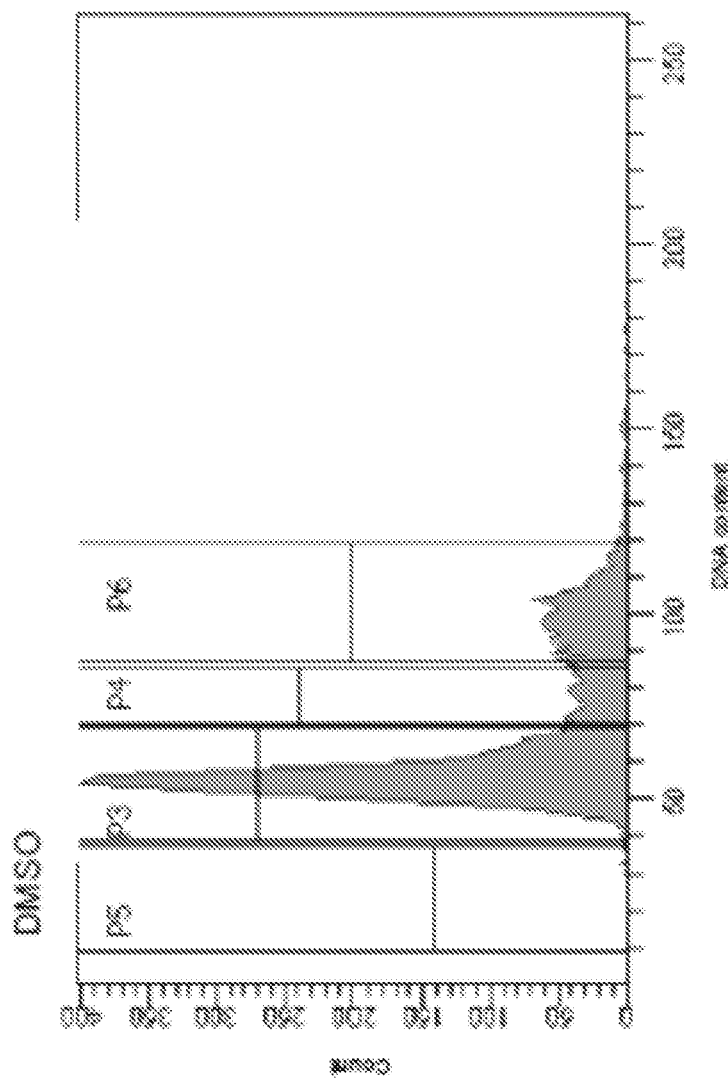
FIGS. 12A and 12B demonstrate the effect of Compound 87 on cell cycle in U87 cells: control (12A), Compound 87 (12B).
Figure 12B:
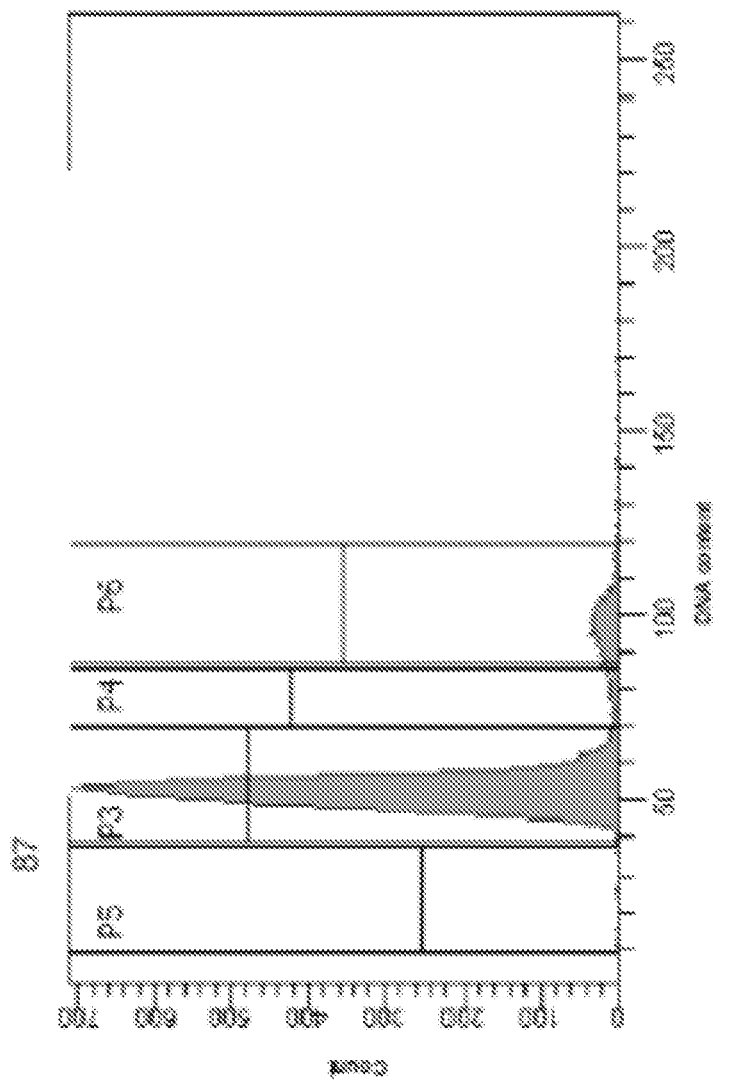
Figure 13A:
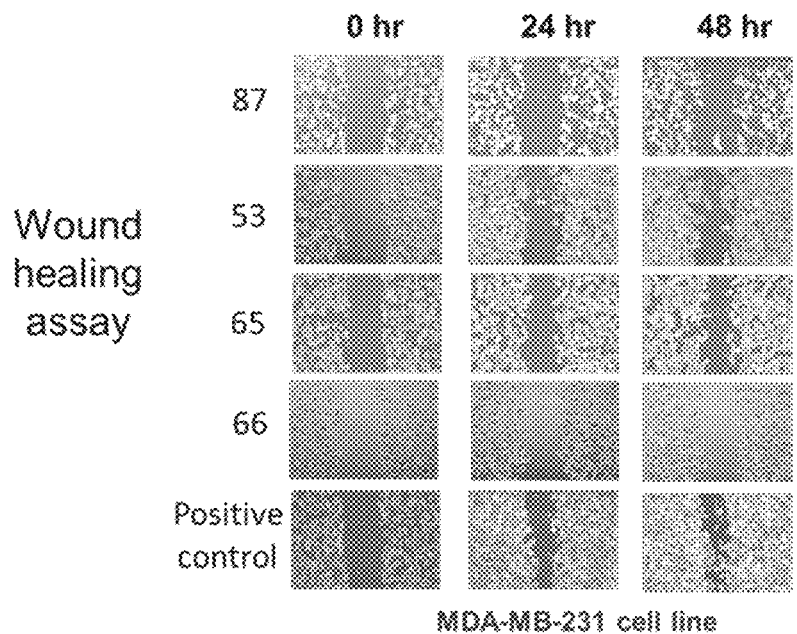
FIGS. 13A-13C show the inhibitory activity of representative Compounds 87, 53, 65, and 66 on the cell migration and invasion of MDA-MB-231 breast cancer cells: wound healing assay (13A), migration (13B), and invasion assay (13C).
Figure 13B:
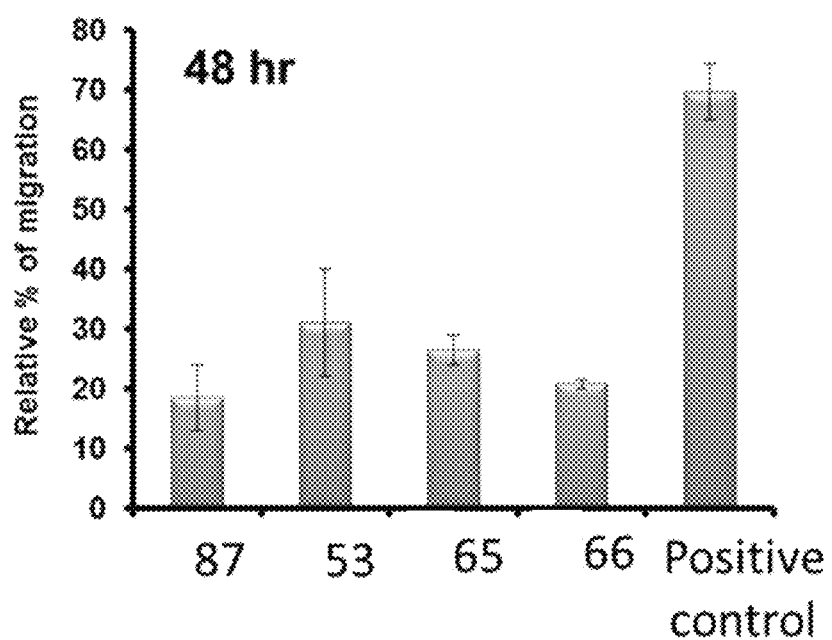
Figure 13C:
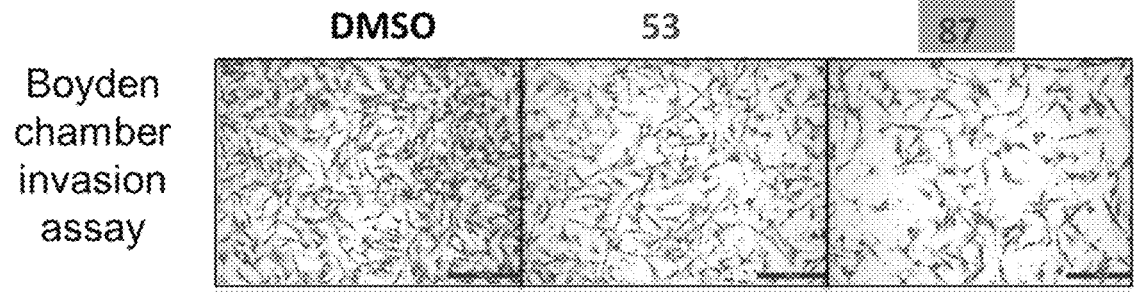

The association of dysfunction of CRAC channel activity with various diseases such as cancer and autoimmune diseases has been validated in the literature. Therefore, in the following experiments, the activity of these compounds was evaluated in different models, and it was found that exemplary compounds of the disclosure, Compounds 53 and 87, significantly inhibit cytokine IL-2 expression in primary T cells, with the calculated $IC_{50}$ of 15.6±1.17 μM and 0.86±0.12 μM respectively (as shown in FIGS. 9A-9F). In addition, the antitumor effect of these compounds was also tested in different cancer cell models, including a leukemia cell line (Jurkat cells), a breast cancer cell line (MDA-MB-231), and a glioma cell line (U87). Compound 87 can induce cell cycle arrest at G0 stage in Jurkat (FIG. 11B) and U87 cells (FIG. 12B) compared to their respective controls (FIGS. 11A and 12A). Compound 53 can also inhibit IL-2 and IFNγ expression in Jurkat cell (FIG. 10). In a wound healing assay, representative compounds of the disclosure, Compounds 53, 65, 66, and 87, can greatly inhibit MDA-MB-231 cell migration (as shown in FIGS. 13A and 13B). Meanwhile, representative compounds of the disclosure, Compounds 53 and 87 can greatly inhibit the MDA-MB-231 cell invasion (FIG. 13C). In the azoxymethane-induced mouse colon cancer model, representative compound of the disclosure, Compound 53, can greatly decrease the number of the formed tumors in the colon, and the activity is also better than the positive control drug CsA (as demonstrated in FIGS. 14A and 14B).

These results indicate that blocking CRAC channel function, e.g., by compounds of Formulae I-III, can produce a therapeutic effect. For example, the compounds in the invention can be particularly useful to treat one or more of the following diseases: 1) immune system diseases, 2) hyperplastic diseases, and 3) cancer. Additionally, in some embodiments, the compounds can be used to suppress or prevent transplant immune rejection reaction.

Thus, in another aspect, disclosed herein is a method of treatment of a condition associated with an abnormal CRAC channel activity in a subject in need thereof, comprising administering to the subject an amount of a CRAC channel inhibitory agent in the amount effective to inhibit CRAC channel, wherein the CRAC channel inhibitory agent is a compound of Formula I, Formula II, or Formula III. In some embodiments, the CRAC channel inhibitor is Compound 41, 53, 62, 63, 64, 65, 66, 69, 79, 86, 87, 98, 99, 100, 101, 102, 103, 106, 111, 112, or 113. In some embodiments, the CRAC channel inhibitor is Compound 53 or 87.

Specifically, the compounds disclosed herein, e.g., compounds of Formulae I, II, or III, can be used to treat the immune system diseases. In some embodiments, the immune system diseases include but are not limited to autoimmune diseases and the related inflammation, such as systemic lupus erythematosus, rheumatoid arthritis, systemic vasculitis, scleroderma, dermatomyositis, multiple sclerosis, autoimmune hemolyticanemia, thyroiditis, ulcerative colitis, eczema, psoriasis, vasculitis, pancreatitis, myasthenia gravis, glomerulonephritis, allergy, allergic inflammation (allergic rhinitis), asthma, uveitis, neurogenic inflammation, and diabetes type 1.

In particular embodiments, the compounds of the invention can be applied to treat hyperplastic diseases, including but not limited to cardiac hypertrophy, benign prostatic hyperplasia, familial adenomatous polyposis, neurofibromatosis, psoriasis, hypertrophic scar, myelodysplastic syndromes, cystic fibrosis, and atherosclerosis hamper.

In other embodiments, the compounds of the invention can be used to treat various types of cancers, including but not limited to leukemia, lymphoma, breast cancer, prostate cancer, liver cancer, lung cancer, colon cancer, skeletal muscle, cervical cancer, nasopharyngeal cancer, epidermoid cancer, esophageal cancer, pancreatic cancer, thyroid cancer, rhabdomyosarcoma, glioma, osteosarcoma, neuroblastoma, astrocytoma, and schwannoma.

In certain embodiments, the compounds of Formulae I, II, or III can suppress the immune rejection in transplant, such as organ, marrow, stem cell, or other tissues or cell transplant.

In other embodiments, the compounds of the Formulae I, II, or III can be used as their pharmaceutically acceptable salts, solvates, or hydrates.

Preparation of pharmaceutical salts is well known to those persons skilled in the art. When there is an acidic group present in the structure of a pharmaceutically active compound, such as the compounds of the present invention, pharmaceutically acceptable salts can be prepared by contacting the compound with a nontoxic inorganic base, including potassium, sodium, calcium, ammonium, lithium, ferric, copper, and magnesium hydroxides. In some embodiments, pharmaceutically acceptable salts can be prepared by contacting the compound with a nontoxic organic base, including but not limited to arginine, betaine, histidine, N-methyl glucamine, lysine, L-glucamine and others. In some embodiments, when a basic group is present in the structure of a pharmaceutically active compound, such as the compounds of the present invention, pharmaceutically acceptable salts can be prepared by contacting the compound with a nontoxic acid, for example, hydrochloric, hydrobromic, sulfuric, acetic, phosphoric, tartaric, citric, fumatric, nitric, gluconic, malic, glutamic, and succinic acids.

Pharmaceutical solvates or hydrates of the compounds of the present invention can be formed by freeze-drying the solutions of the compounds in water or any other suitable solvent, e.g., ethanol, methanol, DMSO, acetic acid, isopropanol, ethyl acetate, ethanolamine. The general methods of preparation of solvates and hydrates method are well known to persons skilled in the art.

In certain embodiments, the compounds of the invention, or their pharmaceutical salts, solvates, or hydrates can be administered in their pure form. However, more typically, it is desirable to administer a pharmaceutical agent in the form of a pharmaceutical composition, wherein the composition comprises the active ingredient and one or more pharmaceutically acceptable carriers or excipients. In some embodiments, inclusion of such carriers or excipients does not affect the activity of compounds in the invention. Specifically, the pharmaceutical carriers include but are not be limited to water, saline, glucose, buffer, glycerol, ethanol, olive oil, peanut oil, and other ingredients. In some embodiments, pharmaceutical excipients include but not to be limited to binders (e.g., dextrin, hydroxypropyl methylcellulose, polyvinyl pyrrolidone), fillers (e.g., lactose, starch, microcrystalline cellulose), disintegrating agents (e.g., croscarmellose sodium), lubricants (e.g., magnesium stearate), glidants (e.g., colloidal silicon dioxide), surfactants (e.g., tween), solubilizers (e.g., PEG), antiseptics, flavoring agents, etc. In some instances, the carriers and/or excipients are compounds or ingredients designated as GRAS by the FDA. Formulation of active pharmaceutical ingredients is well known to the persons skilled in the art.

Suitable pharmaceutical compositions include but not limited to a tablet, a pill, a granule, a capsule, a power, a syrup, an emulsion, a topical cream, a suppository, a suspension, an ointment, an inhalant, a patch, a gel, and an injectable. In some embodiments, the compositions are sustained release formulas. A person skilled in the art is able to select the appropriate type of the pharmaceutical composition and/or formulation depending on the administration route.

The modes of administration include but are not be limited to oral, intravenous, subcutaneous, intramuscular, rectal, and parenteral. The amounts of the active ingredients that can be combined with pharmaceutical carriers or excipients to form single doses vary depending on the host to be treated and the mode of administration. In some instances, the suggested dose can range from about 0.001 mg/kg to about 100 mg/kg each and 1-3 times intake daily. In some embodiments, the active ingredient, e.g., one of the presently described compounds, can also be administered in combination with one or more other pharmaceutical agents to increase the efficacy of the treatment.

EXAMPLES

As can be appreciated from the disclosure above, the present invention has a wide variety of applications. The invention is further illustrated by the following examples, which are only illustrative and are not intended to limit the definition and scope of the invention in any way.

Example 1

Synthesis of Representative Compounds (1) Synthesis of (Z)-methyl 4-(3-((N-methyl-N'-phenylcarbamimidoyl)thio)-2,5-dioxopyrrolidin-1-yl)benzoate

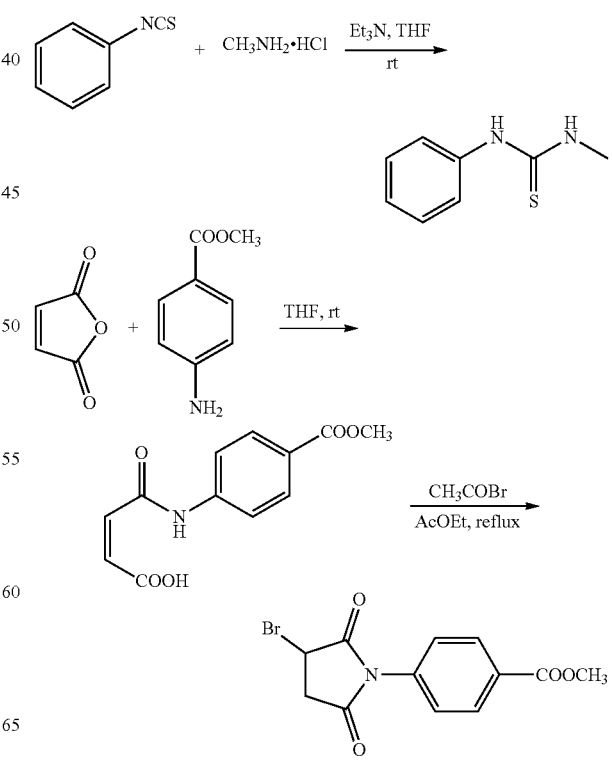

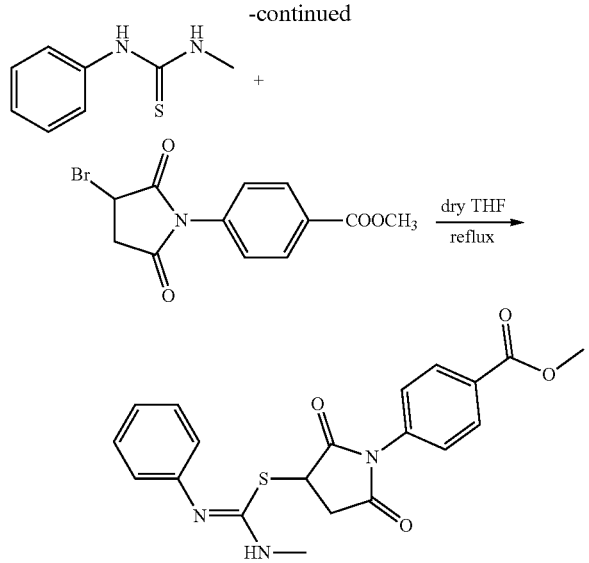

Synthesis of 1-methyl-3-phenylthiourea

To a solution of methylamine hydrochloride (1.35 g) in THF (50 mL), triethylamine (3.06 mL) and phenyl isothiocyanate (2.56 mL) were added respectively, and the mixture was stirred for 5 hrs at room temperature, and then concentrated. The concentrate was purified by column chromatography on silica gel to afford white solid (3.20 g, 96%), m.p. 90-92° C. $^1$H NMR (400 MHz, DMSO): δ (ppm) 9.45 (1H, s), 7.67 (1H, s), 7.32 (4H, m), 7.11 (1H, m), 2.91 (3H, d, J=4.4 Hz); MS (ES) [M+H]$^+$ 167.2.

Synthesis of (Z)-4-((4-(methoxycarbonyl)phenyl)amino)-4-oxobut-2-enoic acid

A mixture of maleic anhydride (1.96 g) and methyl 4-aminobenzoate (3.02 g) in THF (60 mL) was stirred at room temperature for 3 hrs, and the precipitate was filtered off, washed with ethyl acetate and dried to give light yellow powder (4.73 g, 95%), m.p. 190-192° C. $^1$H NMR (400 MHz, DMSO) δ (ppm) 10.63 (1H, s), 7.92 (2H, d, J=8.70 Hz), 7.75 (2H, d, J=8.70 Hz), 6.45 (1H, d, J=12.00 Hz), 6.33 (1H, d, J=12.00 Hz), 4.27 (2H, q), 1.29 (3H, t); MS (ES) [M+H]$^+$ 250.3.

Synthesis of methyl 4-(3-bromo-2,5-dioxopyrrolidin-1-yl)benzoate

Acetyl bromide (0.34 mL) was added to the suspension of (Z)-4-((4-(methoxycarbonyl)phenyl)amino)-4-oxobut-2-enoic acid (996 mg) in ethyl acetate. The mixture was stirred at 30° C. for 2 hrs, and then heated to reflux for 10 hrs. The solvent was concentrated and the residue was purified by column chromatography on silica gel to afford white solid (690 mg, 56%), m.p. 154-156° C. $^1$H NMR (400 MHz, DMSO): δ (ppm) 8.12 (2H, d, J=8.0 Hz), 7.51 (2H, d, J=8.0 Hz), 5.22-5.19 (1H, m), 3.89 (3H, s), 3.66-3.59 (1H, m), 3.21-3.16 (1H, m); MS (ES) [M+H]$^+$ 167.2.

Synthesis of (Z)-methyl 4-(3-((N-methyl-N'-phenylcarbamimidoyl)thio)-2,5-dioxopyrrolidin-1-yl)benzoate The mixture of 1-methyl-3-phenylthiourea (83 mg) and methyl 4-(3-bromo-2,5-dioxopyrrolidin-1-yl)benzoate (156 mg) in THF (3 mL) was stirred at reflux for 6 hrs, and the solvent was concentrated. The residue was purified by column chromatography on silica gel to afford white solid (120 mg, 61%), m.p. 191-192° C. 1H NMR (400 MHz, DMSO): δ (ppm) 7.92 (2H, d, J=8.0 Hz), 7.78 (2H, d, J=8.0 Hz), 7.62 (2H, d, J=8.0 Hz), 7.46 (2H, d, J=8.0 Hz), 7.36-7.30 (2H, m), 7.10 (1H, t, J=8.0 Hz), 6.81 (2H, d, J=8.0 Hz), 4.56-4.53 (1H, m), 4.04-4.01 (2H, m), 3.81 (3H, s), 3.30-3.25 (1H, m), 3.06 (1H, t, J=8.0 Hz), 2.96-2.89 (1H, m); MS (ES) [M+H]+ 398.2.

(2) Synthesis of (Z)-methyl 4-(3-((N'-(2-methoxyphenyl)-N-methylcar-bamimidoyl)thio)-2,5-dioxopyrrolidin-1-yl)benzoate

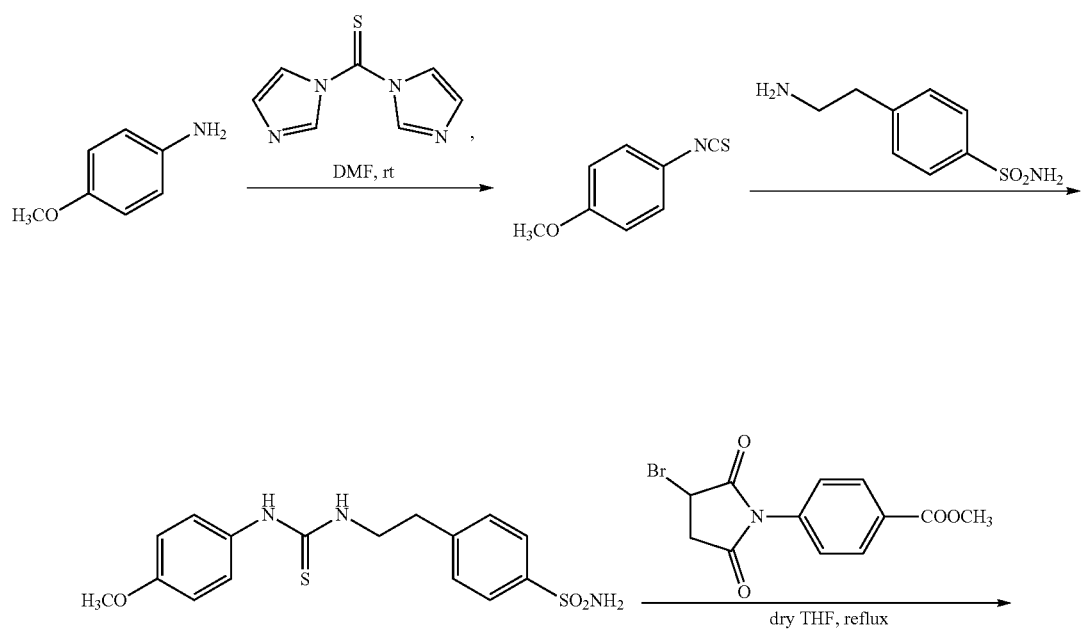

-continued

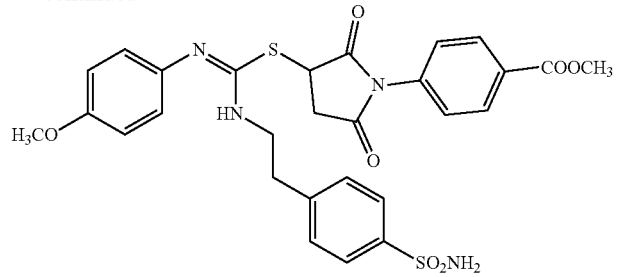

Synthesis of 4-(2-(3-(4-methoxyphenyl)thioureido)ethyl)benzenesulfonamide

To a mixture of 1,1'-thiocarbonyl diimidazole (320 mg) and p-anisidine (180 mg) in DMF (3 mL), 4-(2-aminoethyl)benzenesulfonamide (330 mg) was added, and the mixture was stirred at room temperature for 5 hrs. Then water was added and the mixture was extracted with EtOAc. The organic layers were combined, washed with water and brine respectively, dried over $Na_2SO_4$, filtered, and concentrated in vacuo to give white solid powder (510 mg, 93%), m.p. 160-162° C. $^1$H NMR (400 MHz, DMSO): δ (ppm) 9.61 (s, 1H), 7.86 (s, 1H), 7.76 (d, J=8.0 Hz, 2H), 7.62 (d, J=8.0 Hz, 2H), 7.43 (d, J=8.0 Hz, 2H), 7.31 (s, 2H), 7.19 (d, J=8.0 Hz, 2H), 3.93 (s, 3H), 3.72-3.69 (m, 2H), 2.94 (t, J=7.4 Hz, 2H); MS (ES) $[M+H]^+$ 365.3.

Synthesis of (E)-methyl 4-(3-((N'-(4-methoxyphenyl)-N-(4-sulfamoylphenethyl)-carbamimidoyl)thio)-2,5-dioxopyrrolidin-1-yl)benzoate A mixture of 4-(2-(3-(4-methoxyphenyl)thioureido)ethyl)benzenesulfonamide (183 mg) and methyl 4-(3-bromo-2,5-dioxopyrrolidin-1-yl)benzoate (156 mg) in THF (3 mL) was stirred at reflux for 6 hrs, and the solvent was concentrated. The residue was purified by column chromatography on silica gel to afford white solid (197 mg, 66%), m.p. 176-178° C. $^1$H NMR (400 MHz, DMSO): δ (ppm) 10.49 (1H, s), 7.92 (2H, d, J=8.0 Hz), 7.78 (2H, d, J=8.0 Hz), 7.68 (2H, d, J=8.0 Hz), 7.46 (2H, d, J=8.0 Hz), 7.36-7.30 (2H, m), 6.91 (2H, d, J=8.0 Hz), 6.79 (2H, d, J=8.0 Hz), 4.02 (2H, t, J=8.0 Hz), 3.82 (3H, s), 3.73 (3H, s), 3.31-3.26 (1H, m), 3.06 (1H, t, J=8.0 Hz), 2.96-2.89 (1H, m); MS (ES) $[M+H]^+$ 597.2.

Example 2

Biological Effects of Representative Compounds

Cell Proliferation Assay

The cell proliferation was measured using the WST-1 proliferation assay kit. Briefly, an amount of $5-6\times10^3$ cells per well were seeded in 96-well plates with a total volume of 100 μL. After culturing overnight, cells were treated with varying concentrations of compounds for 24 h at 37° C. with 5% $CO_2$. Then, 10 μL of WST-1 reagents were added to each well and the plate was incubated for another 2 h. The absorbance of each well was measured on a microplate reader at a test wavelength 460 nm. The inhibitory rate was calculated with the following equation: inhibition rate=100%×(OD control well−OD treated well)/(OD control well−OD blank well). Then inhibition curves were fit using GraphPad Prism 5 software and $IC_{50}$ (defined as the drug concentration that required for inhibiting growth by 50% relative to controls) was calculated.

Cell Cycle Analysis

Cells were treated with or without compounds at 37° C. with 5% $CO_2$. After incubation for 24 h, cells were collected by trypsinization and fixed with cold 95% ethanol over 30 min at 4° C. Subsequently, the cell suspension was centrifuged at 1000 rmp/5 min, and washed with PBS one time. The cell pellets were resuspended in 0.4 mL PBS and treated with RNAase A (0.1 mg/mL) at 37° C. for 30 min. Then, propidium iodine (50 μg/mL, PI) was added and the cells were stained for 30 min at 37° C. Analysis of cellular DNA content was performed by flow cytometry.

Migration Assay

The effect of compounds on inhibiting migration was evaluated using wound healing assay. Briefly, cells were seeded in a six well-plate, and a wound was generated by scratching the cell monolayer with a 200 μL pipette tip. Then, cells were continued to be cultured in the presence or absence of compounds, and the photographic recording was performed at 0 h, 24 h, and 48 h respectively. The number of the migrated cells was calculated with ImageJ software.

Effect of Compounds on Cytokine Expression

The lymph nodes and a spleen from mouse were collected, and then the immune cells were induced to differentiate towards Th1 cells in presence of α-CD3, α-CD28, IL-12, and IL-2. After obtaining Th1 cells, the cells were amplified and then the cells were treated with drugs. The expression level of the cytokine was analyzed using flow cytometry.

Figure 14A:
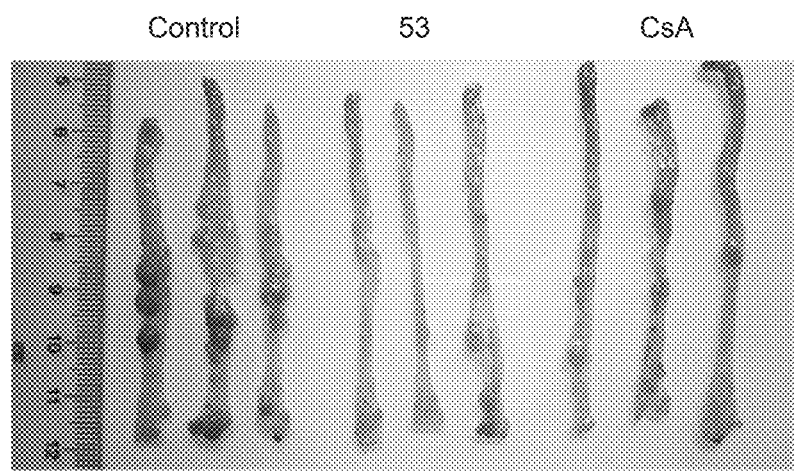
FIGS. 14A and 14B demonstrate that Compound 53 has antitumor activity in the azoxymethane (AOM)-induced mouse colon cancer model by reducing the number of tumors formed compared to untreated control group and group treated with a known anti-cancer agent CsA.
Figure 14B:
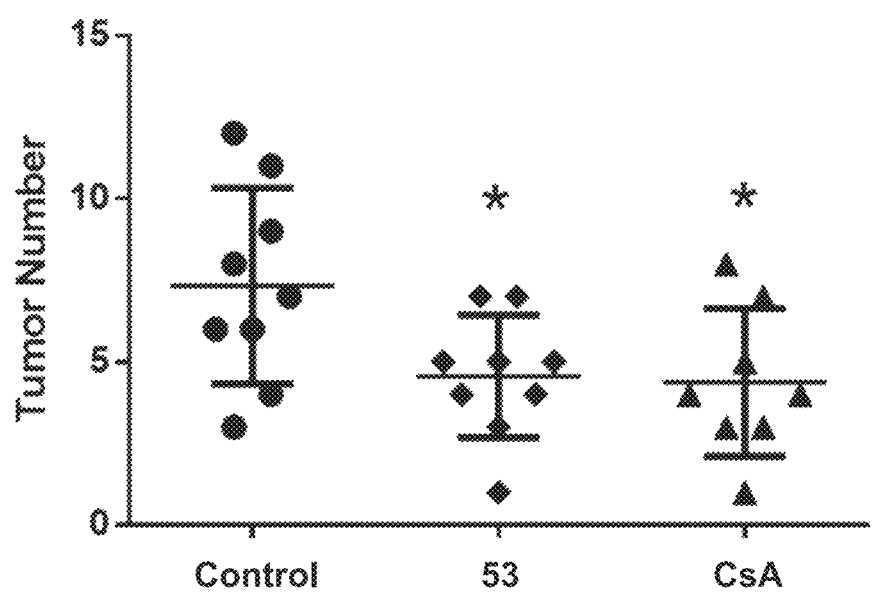

Antitumor Effect of Compounds on Azoxymethane (AOM)-Induced Mouse Colon Cancer Model To induce colon cancer in situ, mice (four month old) were randomly divided into three groups: (1) AOM control group; (2) Compound 53 group, (3) CsA group, and injected with AOM subcutaneously (10 mg/kg body weight) once a week for 4 weeks. Then, Compound 53 and CsA group were treated with Compound 53 and CsA respectively for 8 weeks, and the control group was treated with 0.9% NaCl solution. Then, mice were killed and the colon was isolated. The number of the tumors formed was analyzed. Representative results are shown in FIGS. 14A and 14B, demonstrating that Compound 53, an exemplary CRAC inhibitor, demonstrated activity in this in vivo model by reducing the number of tumors formed compared to the control group.

While illustrative embodiments have been illustrated and described, it will be appreciated that various changes can be made therein without departing from the spirit and scope of the invention.

The invention claimed is:

1. A method of treatment of a disease, disorder, or condition treatable by inhibiting calcium release-activated calcium (CRAC) channel, comprising administering to a subject in need thereof an amount of a CRAC channel inhibitor effective to inhibit CRAC channel, wherein the CRAC channel inhibitor is a compound of Formula I:

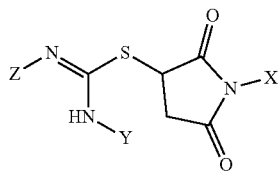

(I)

or a pharmaceutically acceptable salt, solvate, or a hydrate thereof, wherein

X is a phenyl substituted with one, two, or three groups selected from optionally substituted C1-C6 alkyl, carboxyl, alkoxycarbonyl, and amido group;

Y is an optionally substituted C1-C8 alkyl, an optionally substituted C6-C10 aryl-C1-C8 alkyl, an optionally substituted C5-C10 heteroaryl-C1-C8 alkyl, an optionally substituted C3-C10 heteroalkyl, an optionally substituted C3-C6 heterocyclyl, an optionally substituted C6-C10 aryl, or an optionally substituted C5-C10 heteroaryl; and Z is an optionally substituted C6-C10 aryl or an optionally substituted C5-C10 heteroaryl.

2. The method of claim 1, wherein the compound of Formula I has the structure of Formula II:

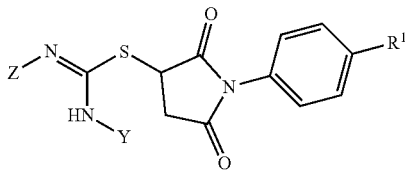

(II)

wherein $R^1$ is an optionally substituted C1-C6 alkyl, COOH, $COOR^2$, $CONH_2$, or $CONHR^2$;

$R^2$ is an optionally substituted C1-C6 alkyl;

Y is an optionally substituted C1-C8 alkyl, an optionally substituted C6-C10 aryl-C1-C8 alkyl, or an optionally substituted C5-C10 heteroaryl-C1-C8 alkyl; and Z is an optionally substituted C6-C10 aryl or an optionally substituted C5-C10 heteroaryl.

3. The method of claim 1, wherein the compound of Formula I has the structure of Formula III:

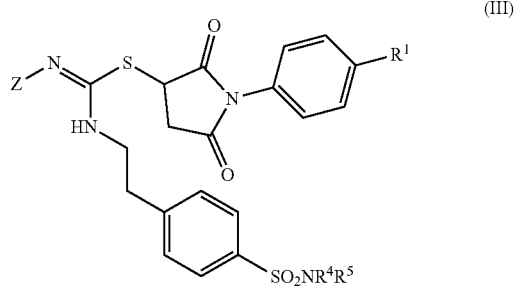

(III)

wherein $R^1$ is COOH, $COOR^2$, or $CONHR^2$;

$R^2$ is an optionally substituted C1-C6 alkyl;

$R^4$ is H or an optionally substituted C1-C6 alkyl;

$R^5$ is H or an optionally substituted C1-C6 alkyl; and

Z is an optionally substituted C6-C10 aryl or an optionally substituted C5-C10 heteroaryl.

4. The method of claim 1, wherein Y is methyl, ethyl, propyl, n-butyl, tert-butyl, cyclopropyl, phenyl, benzyl, 4-methoxybenzyl, 3,4-dimethoxyphenyl, 4-sulfonamidophenethyl, or 5-methylbenzo[d][1,3]dioxolyl.

5. The method of claim 1, wherein Z is phenyl, 4-halophenyl, 3-trifluoromethyl-phenyl, 2,5-dichlorophenyl, 3-chloro-4-methyl-phenyl, 2-methoxy-phenyl, 4-methoxycarbonyl-phenyl, benzo[d][1,3]dioxolyl, 3,5-dichlorophenyl, 3-methoxyphenyl, or 3-halophenyl.

6. The method of claim 1, wherein the compound is:

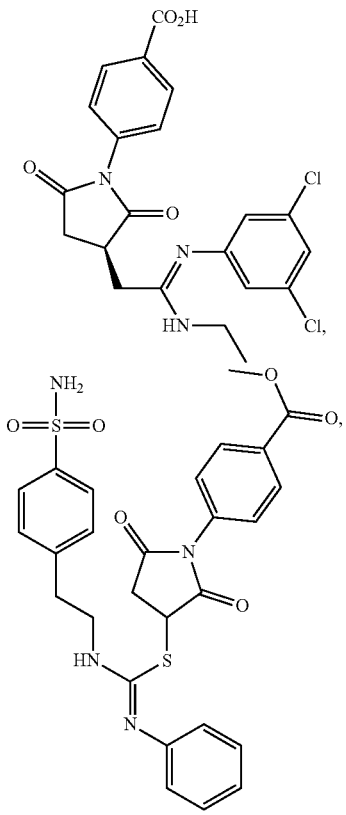

69
-continued
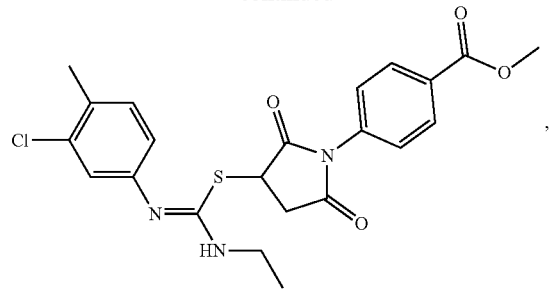
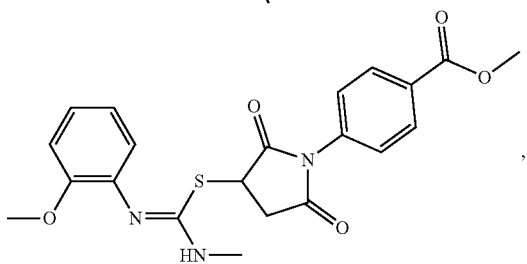
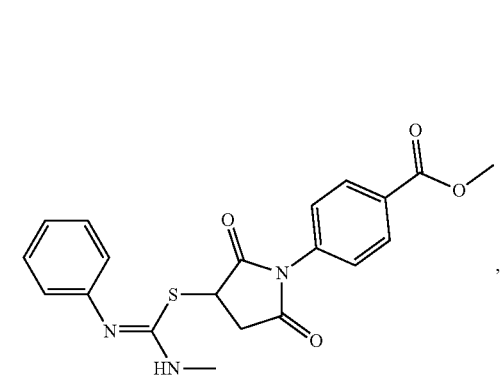
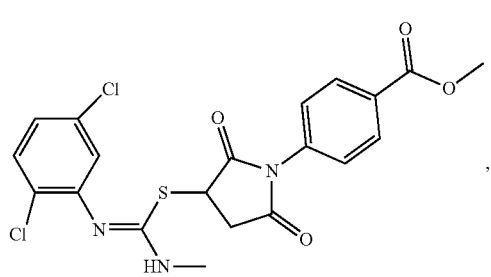
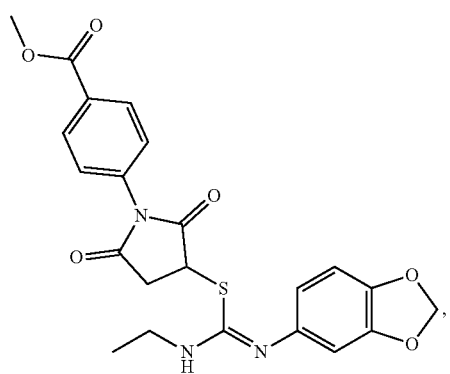
70
-continued
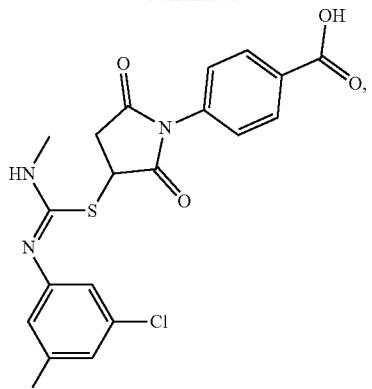
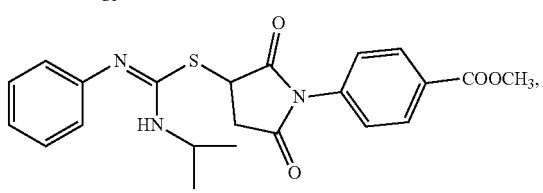
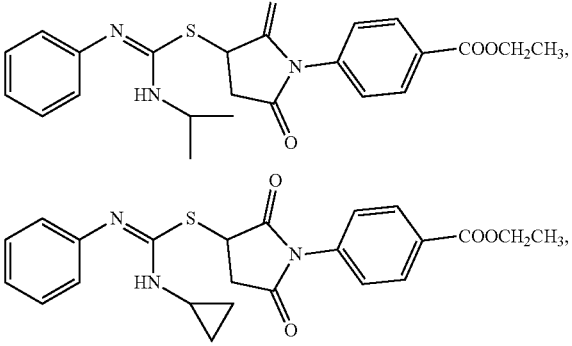
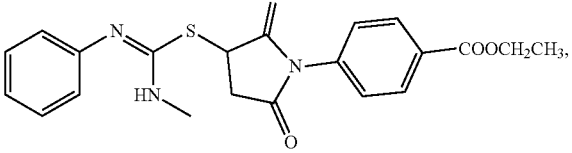
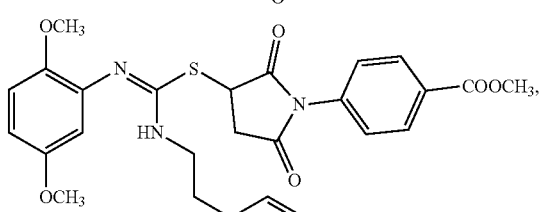
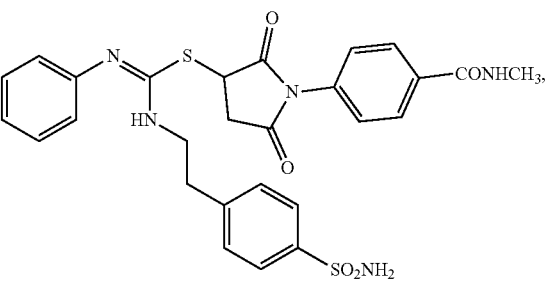

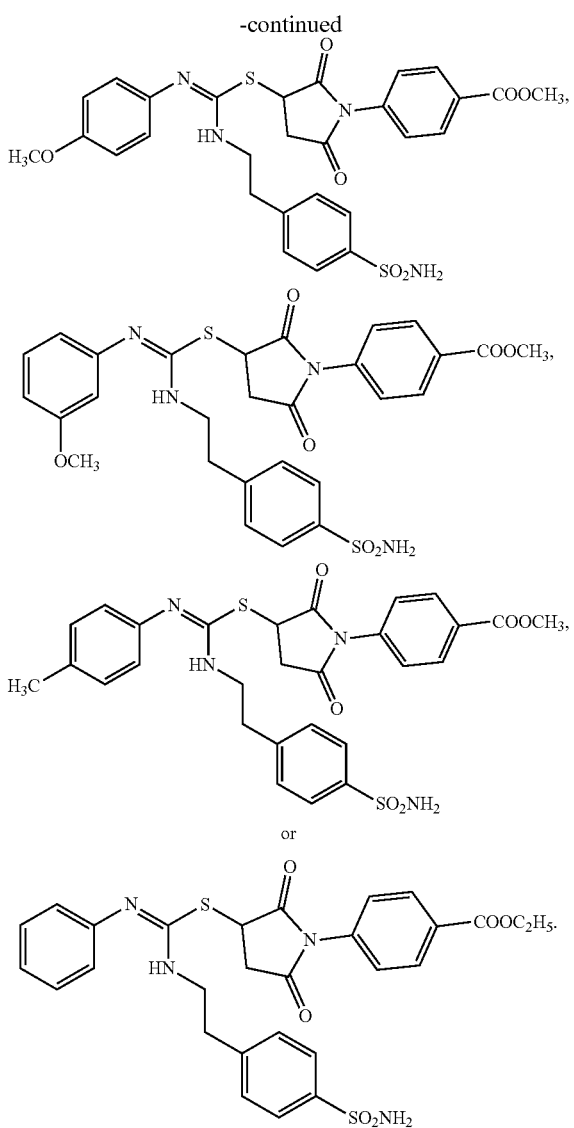

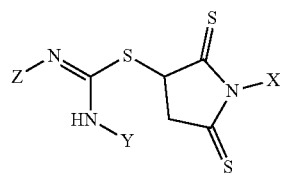

(I)

or a pharmaceutically acceptable salt, solvate, or a hydrate thereof, wherein X is a phenyl substituted with one, two, or three groups selected from optionally substituted C1-C6 alkyl, carboxyl, alkoxycarbonyl, and amido group;

Y is an optionally substituted C1-C8 alkyl, an optionally substituted C6-C10 aryl-C1-C8 alkyl, an optionally substituted C5-C10 heteroaryl-C1-C8 alkyl, an optionally substituted C3-C10 heteroalkyl, an optionally substituted C3-C6 heterocyclyl, an optionally substituted C6-C10 aryl, or an optionally substituted C5-C10 heteroaryl; and Z is an optionally substituted C6-C10 aryl or an optionally substituted C5-C10 heteroaryl.

13. The method of claim 12, wherein the compound of Formula I has the structure of Formula II:

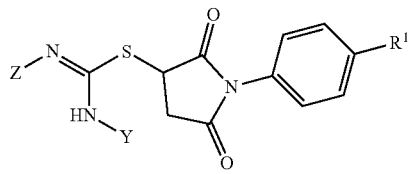

(II)

wherein

R$^1$ is an optionally substituted C1-C6 alkyl, COOH, COOR$^2$, CONH$_2$, or CONHR$^2$;

R$^2$ is an optionally substituted C1-C6 alkyl;

Y is an optionally substituted C1-C8 alkyl, an optionally substituted C6-C10 aryl-C1-C8 alkyl, or an optionally substituted C5-C10 heteroaryl-C1-C8 alkyl; and Z is an optionally substituted C6-C10 aryl or an optionally substituted C5-C10 heteroaryl.

14. The method of claim 12, wherein Y is an optionally substituted phenethyl.

15. The method of claim 12, wherein the compound of Formula I has the structure of Formula III:

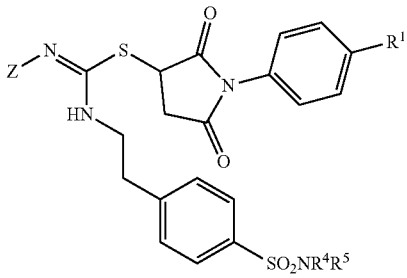

(III)

wherein

R$^1$ is H, COOH, COOR$^2$, or CONHR$^2$;

R$^2$ is an optionally substituted C1-C6 alkyl;

7. The method of claim 1, wherein the disease, disorder, or condition treatable by inhibiting CRAC channel is an immune system disease, a hyperplastic disease, or cancer.

8. The method of claim 1, wherein the disease, disorder, or condition treatable by inhibiting CRAC channel is colon cancer, breast cancer, leukemia, or glioma.

9. The method of claim 1, wherein the disease, disorder, or condition treatable by inhibiting CRAC channel is an organ or a tissue transplant rejection.

10. The method of claim 1, wherein the disease, disorder, or condition treatable by inhibiting CRAC channel is an immunodeficiency disorder, overactive immune response, allergy, or autoimmune disorder.

11. The method of claim 1, wherein the disease, disorder, or condition treatable by inhibiting CRAC channel is a condition induced by an overactive immune recognition.

12. A method of selective suppression of immune function or response, comprising administering to a subject in need thereof an amount of a calcium release-activated calcium (CRAC) channel inhibitor effective to inhibit CRAC channel, wherein the CRAC channel inhibitor is a compound of Formula I:

$R^4$ is H or an optionally substituted C1-C6 alkyl;
$R^5$ is H or an optionally substituted C1-C6 alkyl; and
Z is an optionally substituted C6-C10 aryl or an optionally substituted C5-C10 heteroaryl.
16. The method of claim 12, wherein the compound is:
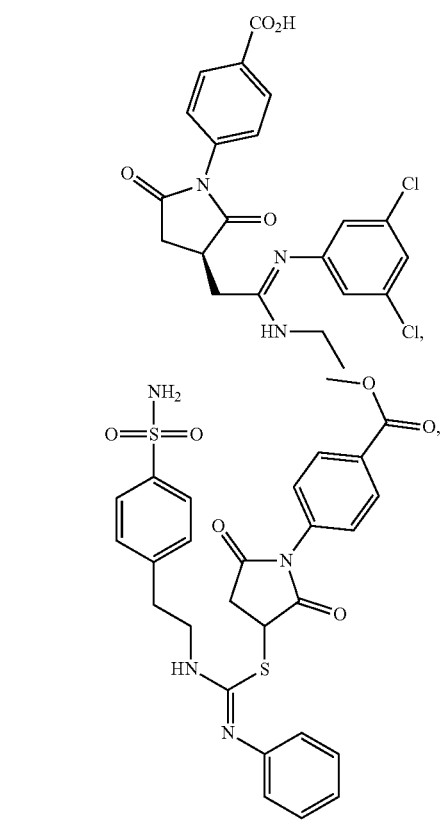
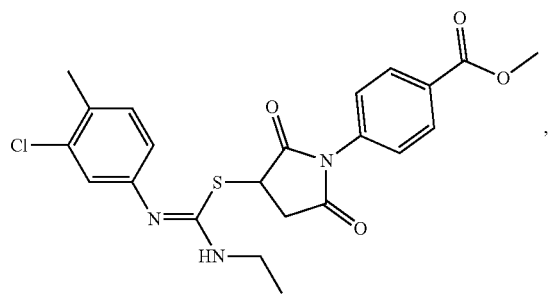
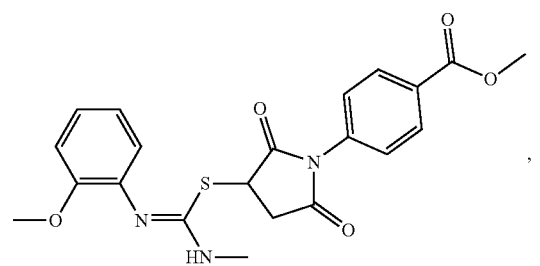
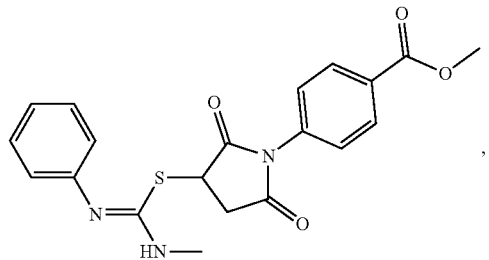
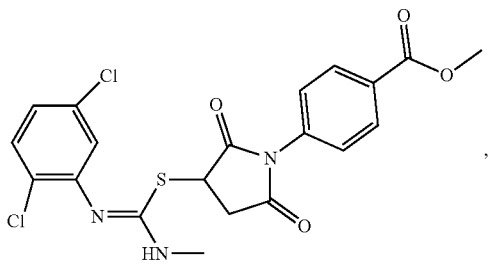
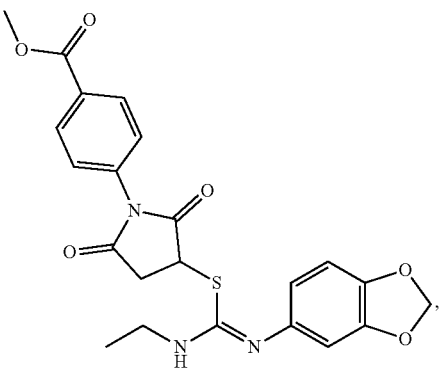
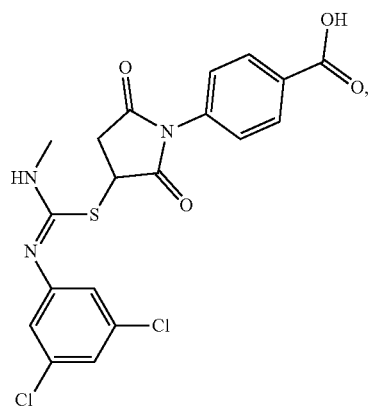
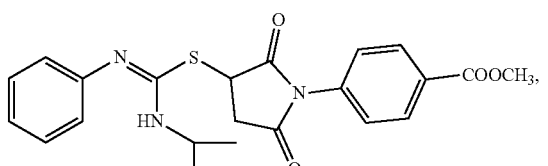
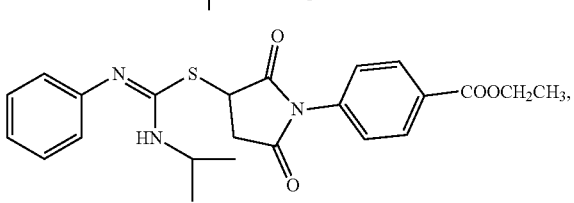

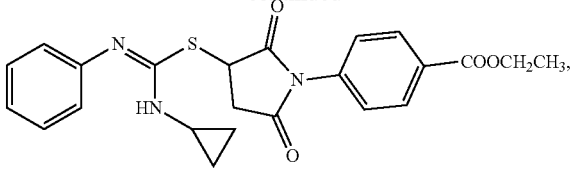

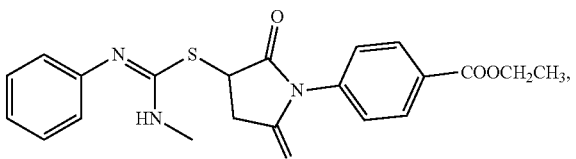

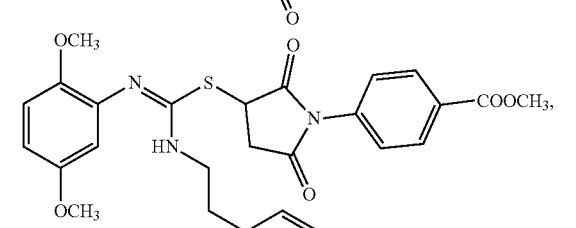

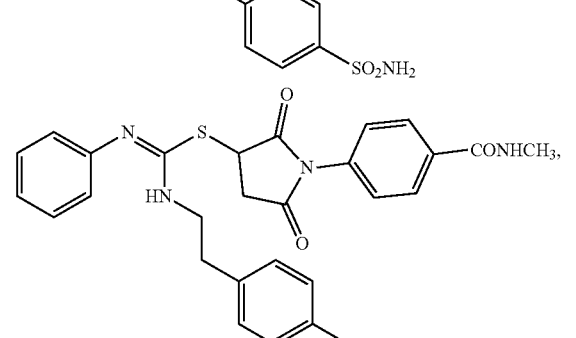

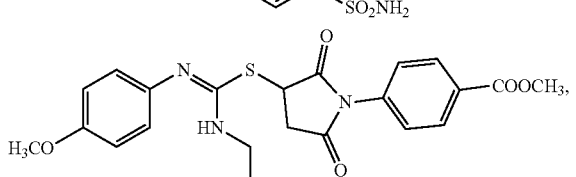

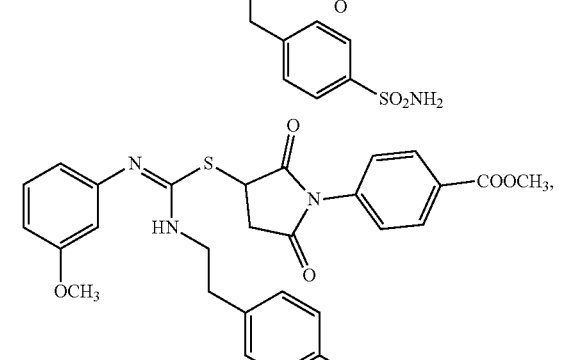

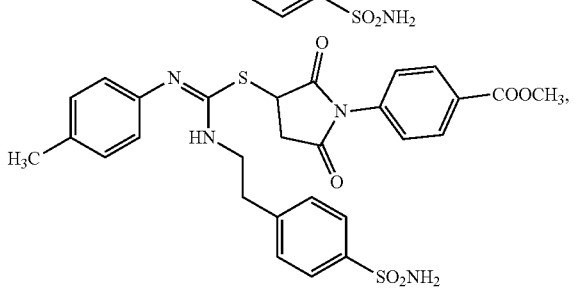

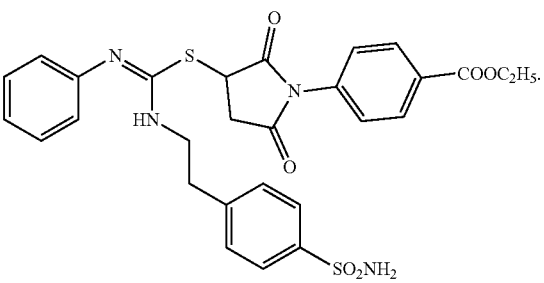

17. A method of treatment of a disease, disorder, or condition treatable by inhibiting calcium release-activated calcium (CRAC) channel, comprising administering to a subject in need thereof an amount of a CRAC channel inhibitor effective to inhibit CRAC channel, wherein the CRAC channel inhibitor is a compound of Formula I:

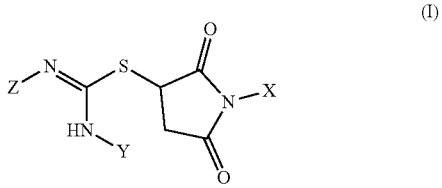

(I)

or a pharmaceutically acceptable salt, solvate, or a hydrate thereof, wherein
X is an optionally substituted C6-C10 aryl or an optionally substituted C5-C10 heteroaryl;
Y is an optionally substituted phenethyl; and
Z is an optionally substituted C6-C10 aryl or an optionally substituted C5-C10 heteroaryl.

18. The method of claim 17, wherein the compound of Formula I has the structure of Formula III:

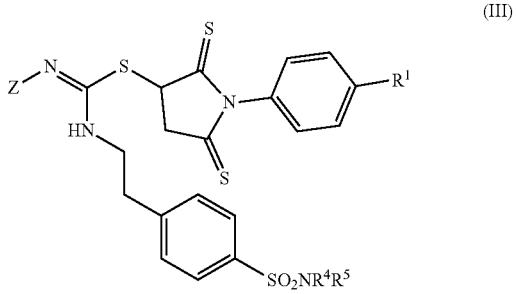

(III)

wherein
R¹ is H, COOH, COOR², or CONHR²;
R² is an optionally substituted C1-C6 alkyl;
R⁴ is H or an optionally substituted C1-C6 alkyl;
R⁵ is H or an optionally substituted C1-C6 alkyl; and
Z is an optionally substituted C6-C10 aryl or an optionally substituted C5-C10 heteroaryl.

19. The method of claim 17, wherein Z is phenyl, 4-halophenyl, 3-trifluoromethyl-phenyl, 2,5-dichlorophenyl, 3-chloro-4-methyl-phenyl, 2-methoxy-phenyl, 4-methoxycarbonyl-phenyl, benzo[d][1,3]dioxolyl, 3,5-dichlorophenyl, 3-methoxyphenyl, or 3-halophenyl.

20. The method of claim 17, wherein the compound is:

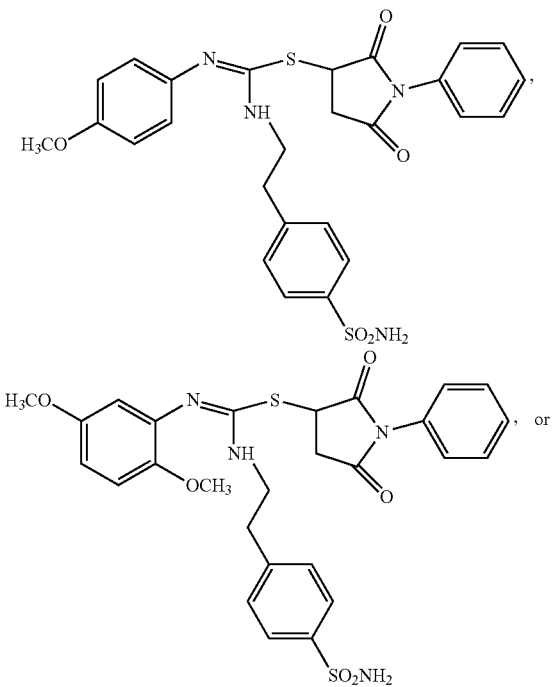

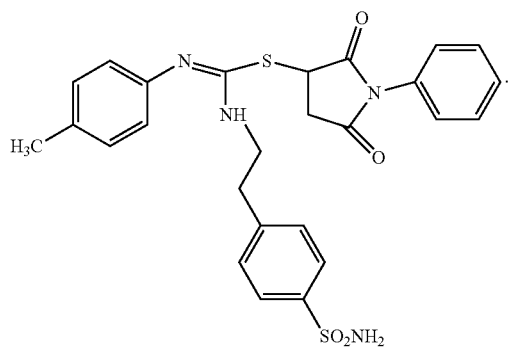

21. The method of claim 17, wherein the disease, disorder, or condition treatable by inhibiting CRAC channel is an organ or a tissue transplant rejection.

22. The method of claim 17, wherein the disease, disorder, or condition treatable by inhibiting CRAC channel is an immunodeficiency disorder, overactive immune response, allergy, or autoimmune disorder.

23. The method of claim 17, wherein the disease, disorder, or condition treatable by inhibiting CRAC channel is a condition induced by an overactive immune recognition.

* * * * *